(12) United States Patent
Joye et al.

(10) Patent No.: US 7,081,112 B2
(45) Date of Patent: *Jul. 25, 2006

(54) CRYOGENICALLY ENHANCED INTRAVASCULAR INTERVENTIONS

(75) Inventors: James Joye, Monte Sereno, CA (US); Kristine Tatsutani, Oakland, CA (US); Ronald Williams, Menlo Park, CA (US); Richard S. Williams, Redwood City, CA (US)

(73) Assignee: Cryovascular Systems, Inc., Los Gatos, CA (US)

( * ) Notice: Subject to any disclaimer, the term of this patent is extended or adjusted under 35 U.S.C. 154(b) by 128 days.

This patent is subject to a terminal disclaimer.

(21) Appl. No.: 10/215,357

(22) Filed: Aug. 7, 2002

(65) Prior Publication Data

US 2003/0109912 A1    Jun. 12, 2003

Related U.S. Application Data

(63) Continuation of application No. 09/511,191, filed on Feb. 23, 2000, now Pat. No. 6,468,297.

(60) Provisional application No. 60/121,637, filed on Feb. 24, 1999, provisional application No. 60/169,109, filed on Dec. 6, 1999.

(51) Int. Cl.
    *A61B 18/18* (2006.01)
(52) U.S. Cl. ......................... 606/21; 607/113
(58) Field of Classification Search ............ 607/113, 607/105, 96; 606/20–26; 128/898
See application file for complete search history.

(56) References Cited

U.S. PATENT DOCUMENTS

| 3,827,436 | A |  | 8/1974  | Stumpf et al. |
| 5,577,387 | A |  | 11/1996 | Maytal |
| 5,779,698 | A |  | 7/1998  | Clayman et al. |
| 5,800,486 | A |  | 9/1998  | Thome et al. |
| 5,868,735 | A | * | 2/1999  | Lafontaine ............... 606/21 |
| 5,899,897 | A |  | 5/1999  | Rabin et al. |
| 5,899,898 | A |  | 5/1999  | Arless et al. |
| 5,899,899 | A |  | 5/1999  | Arless et al. |

(Continued)

FOREIGN PATENT DOCUMENTS

WO    WO 98/37822    9/1998

OTHER PUBLICATIONS

U.S. Appl. No. 09/203,011 filed on Dec. 1, 1998 entitled *Apparatus and Method for Cryogenic Inhibition of Hyperplasia*, Inventors: James Joye et al.

Primary Examiner—Michael Peffley
Assistant Examiner—Pete Vrettakos
(74) Attorney, Agent, or Firm—Vidas, Arrett, Steinkraus

(57) ABSTRACT

The invention provides techniques and devices for treating atherosclerotic disease using controlled cryogenic cooling, often in combination with angioplusty. The efficacy of endolusninal cryogenic cooling is enhanced by cooling of target tissues using an insulated cryogenic balloon, the Insulation ideally comprising a fluid which undergoes a phase change at a predetermined temperature. A combination cryogenic/angioplasty catheter avoids exchange procedures between dilation of a stenotic region within a vessel wall and the application of cryogenic cooling. The combination angioplasty/cryogenic cooling catheter may cool the diseased blood vessel before, during, and/or after dilation. Controlled cooling of the vessel wall may change its mechanical properties, weakening the vessel and allowing it to be expanded at a much lower pressure than with conventional uncooled angioplasty. Similar reductions in restenosis may be provided for other primary treatments of the blood vessel, including directional arthrectomy, rotational arthrectomy, laser angioplasty, stenting, and the like.

7 Claims, 13 Drawing Sheets

U.S. PATENT DOCUMENTS

| | | | |
|---|---|---|---|
| 5,971,979 A * | 10/1999 | Joye et al. | 606/21 |
| 5,980,563 A | 11/1999 | Tu et al. | |
| 6,036,689 A | 3/2000 | Tu et al. | |
| 6,129,725 A | 10/2000 | Tu et al. | |
| 6,241,718 B1 | 6/2001 | Arless et al. | |
| 6,283,959 B1 * | 9/2001 | Lalonde et al. | 606/21 |
| 6,537,271 B1 * | 3/2003 | Murray et al. | 606/21 |
| 6,551,274 B1 * | 4/2003 | Heiner | 604/113 |

* cited by examiner

Expansion of N₂O from 500 psi and 0C

| Starting Conditions | | | | | | Final Conditions | | | |
|---|---|---|---|---|---|---|---|---|---|
| Press (kPa) | Press (psia) | Temp (K) | Temp (C) | Density kgmole/m3 | Vapor (%) | Press (kPa) | Press (psia) | Temp (K) | Temp (C) | Vapor (%) |
| 3447 | 500 | 273.18 | 0 | 20.62 | 0 | 101.325 | 14.696 | 184.59 | -88.59 | 44.03 |
| 3447 | 500 | 273.18 | 0 | 20.62 | 0 | 137.9 | 20 | 189.92 | -83.26 | 42.35 |
| 3447 | 500 | 273.18 | 0 | 20.62 | 0 | 172.4 | 25 | 194.01 | -79.17 | 41.03 |
| 3447 | 500 | 273.18 | 0 | 20.62 | 0 | 206.8 | 30 | 197.50 | -75.68 | 39.87 |
| 3447 | 500 | 273.18 | 0 | 20.62 | 0 | 275.8 | 40 | 203.33 | -69.85 | 37.89 |
| 3447 | 500 | 273.18 | 0 | 20.62 | 0 | 344.7 | 50 | 208.12 | -65.06 | 36.19 |
| 3447 | 500 | 273.18 | 0 | 20.62 | 0 | 413.7 | 60 | 212.23 | -60.95 | 34.68 |
| 3447 | 500 | 273.18 | 0 | 20.62 | 0 | 482.6 | 70 | 215.86 | -57.32 | 33.32 |
| 3447 | 500 | 273.18 | 0 | 20.62 | 0 | 551.6 | 80 | 219.12 | -54.06 | 32.05 |
| 3447 | 500 | 273.18 | 0 | 20.62 | 0 | 620.5 | 90 | 222.09 | -51.09 | 30.87 |
| 3447 | 500 | 273.18 | 0 | 20.62 | 0 | 689.5 | 100 | 224.83 | -48.35 | 29.74 |

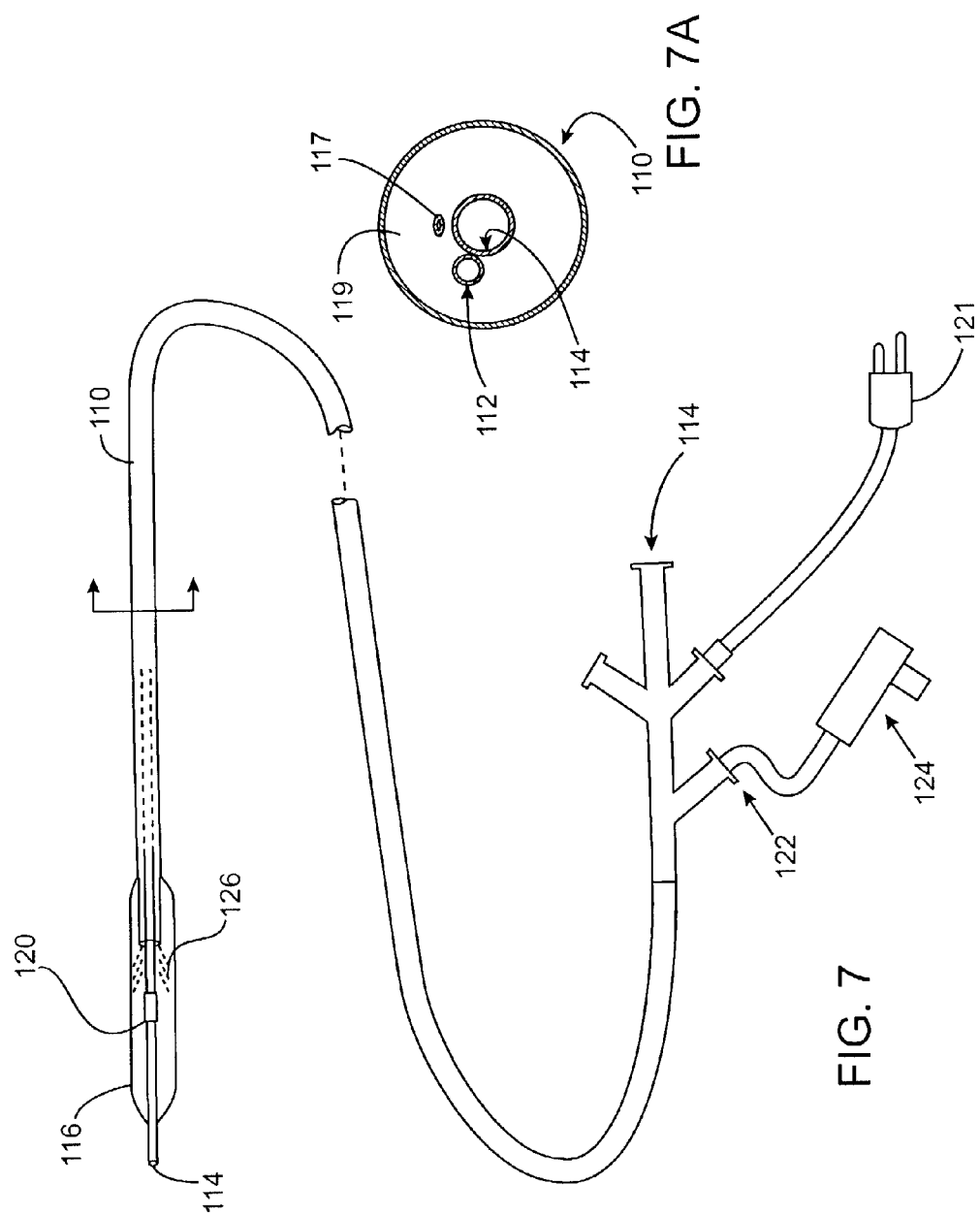

FIG. 11A

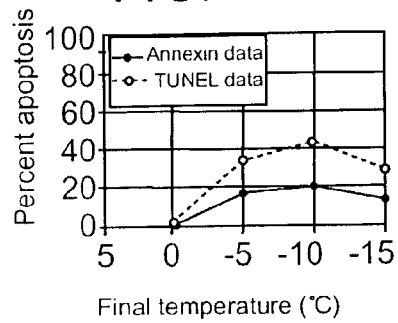

Apoptosis vs. final temperature
for human coronary artery endothelial cells
after 60 second, single cycle freeze.

FIG. 11B

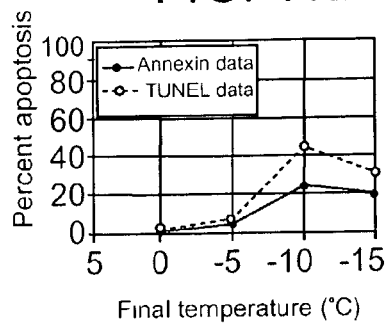

Apoptosis vs. final temperature
for rat arterial smooth muscle cells after
60 second, single cycle freeze

FIG. 11C

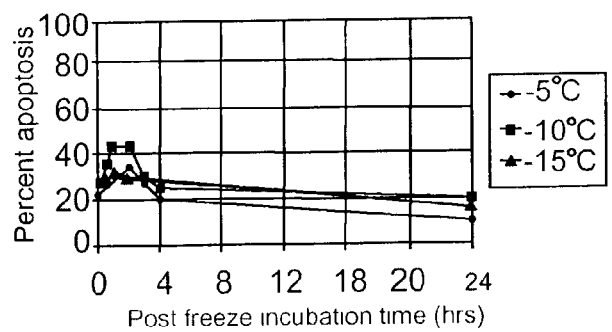

Apoptosis vs. incubation time for
human coronary artery endothelial cells after
60 second, single cycle freeze; TUNEL results.

FIG. 11D

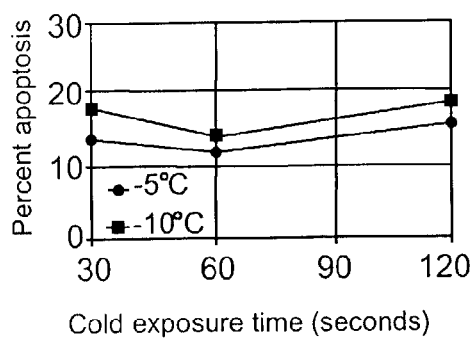

Apoptosis vs exposure time
for human coronary artery endothelial cells
1 hour after single cycle freeze to -5 and
-10°C; Annexin results.

FIG. 11E

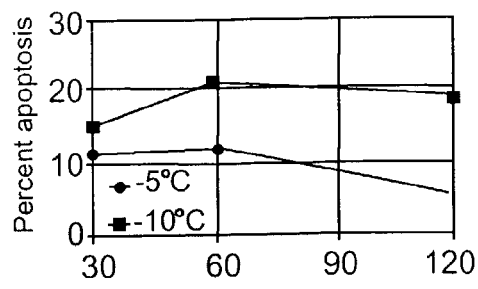

Apoptosis vs. exposure time
for rat arterial smooth muscle cells 1 hour
after single cycle freeze to -5 and -10°C;
Annexin results.

Animal Log
*Cryotherapy*

| ANIMAL ID | Study Dates | | | Treatment | | |
|---|---|---|---|---|---|---|
| | stent injury | treatment | follow up | LAD | LCX | RCA |
| 1. 526 | Day 0 | Day 28 | Day 56 | I | II | I |
| 2. 527 | 0 | 28 | sudden death 28 | II | | I |
| 3. 528 | 0 | 32 | 56 | I | | II |
| 4. 529 | 1 | 32 | 62 | II | I | I |
| 5. 530 | 1 | 33 | 62 | I | I | II |
| 6. 531 | 5 | 70 | 62 | II | | I |
| 7. 560 | 40 | 70 | 98 | I | II | I |
| 8. 558 | 40 | 70 | 98 | I | II | I |
| 9. 559 | 40 | 70 | 98 | I | I | II |

FIG. 12A

Double Stent Injury Model

| | Mean | Std Dev | Std Error | Count | Minuimum | Maximum | # Missing |
|---|---|---|---|---|---|---|---|
| BL Ref, Total | 2.742 | .377 | .080 | 22 | 2.140 | 3.520 | 0 |
| BL Ref, Control | 2.796 | .486 | .172 | 8 | 2.300 | 3.520 | 0 |
| BL, Ref, Cryo | 2.711 | .315 | .084 | 14 | 2.140 | 3.330 | 0 |
| BL MLD, Total | 1.975 | .507 | .108 | 22 | .750 | 2.820 | 0 |
| BL MLD, Control | 2.039 | .598 | .211 | 8 | 1.100 | 2.820 | 0 |
| BL MLD, Cryo | 1.939 | .468 | .125 | 14 | .750 | 2.580 | 0 |
| BL %DS, Total | 28.500 | 14.950 | 3.187 | 22 | 4.000 | 72.000 | 0 |
| BL %DS, Control | 27.875 | 13.705 | 4.846 | 8 | 14.000 | 55.000 | 0 |
| BL %DS, Cryo | 28.857 | 16.110 | 4.305 | 14 | 4.000 | 72.000 | 0 |
| Balloon, Total | 2.880 | .333 | .071 | 22 | 2.440 | 3.660 | 0 |
| Balloon, Control | 3.039 | .235 | .083 | 8 | 2.680 | 3.280 | 0 |
| Balloon, Cryo | 2.794 | .355 | .095 | 14 | 2.440 | 3.660 | 0 |
| Balloon/Artery, Total | 1.065 | .145 | .031 | 22 | .780 | 1.370 | 0 |
| Balloon/Artery, Control | 1.109 | .146 | .052 | 8 | .920 | 1.350 | 0 |
| Balloon/Artery, Cryo | 1.040 | .143 | .038 | 14 | .780 | 1.370 | 0 |
| Post Ref, Total | 2.741 | .373 | .080 | 22 | 2.090 | 3.350 | 0 |
| Post Ref, Control | 2.723 | .459 | .162 | 8 | 2.100 | 3.320 | 0 |
| Post Ref, Cryo | 2.752 | .334 | .089 | 14 | 2.090 | 3.350 | 0 |
| Post MLD, Total | 2.465 | .313 | .067 | 22 | 1.850 | 3.120 | 0 |
| Post MLD, Control | 2.534 | .390 | .138 | 8 | 1.870 | 3.120 | 0 |
| Post MLD, Cryo | 2.425 | .268 | .072 | 14 | 7.850 | 2.770 | 0 |
| Post %DS, Total | 9.955 | 9.383 | 2.001 | 22 | -7.000 | 27.000 | 0 |
| Post %DS, Control | 6.750 | 8.940 | 3.161 | 8 | -7.000 | 20.000 | 0 |
| Post %DS, Cryo | 11.786 | 9.448 | 2.525 | 14 | -4.000 | 27.000 | 0 |
| FU REF, Total | 2.764 | .384 | .082 | 22 | 2.010 | 3.280 | 0 |
| FU REF, Control | 2.849 | .248 | .088 | 8 | 2.390 | 3.080 | 0 |
| FU REF, Cryo | 2.715 | .445 | .119 | 14 | 2.010 | 3.280 | 0 |
| FU MLD, Total | 1.655 | .690 | .147 | 22 | .560 | 3.280 | 0 |
| FU MLD, Control | 1.399 | .660 | .233 | 8 | .560 | 2.430 | 0 |
| FU MLD, Cryo | 1.801 | .686 | .183 | 14 | .990 | 3.280 | 0 |
| FU % DS, Total | 40.455 | 23.122 | 4.930 | 22 | -8.000 | 78.000 | 0 |
| FU % DS, Control | 51.750 | 22.487 | 7.950 | 8 | 18.000 | 78.000 | 0 |
| FU % DS, Cryo | 34.000 | 21.633 | 5.782 | 14 | -8.000 | 69.000 | 0 |

FIG. 12B

ANOVA Table for FU REF
Inclusion criteria: Criteria 1 from      angio data

|  | DF | Sum of Squares | Mean Square | F-Value | P-Value |
|---|---|---|---|---|---|
| Treatment | 1 | .091 | .091 | .607 | .4451 |
| Residual | 20 | 3.002 | .150 | | |

Model II estimate of between component variance •

Fisher's PLSD for FU REF
Effect: Treatment
Significance Level: 5 %
Inclusion criteria: Criteria 1 from      angio data

|  | Mean Diff. | Crit. Diff. | P-Value |
|---|---|---|---|
| Control, Cryo | .134 | .358 | .4451 |

ANOVA Table for FU MLD
Inclusion criteria: Criteria 1 from      angio data

|  | DF | Sum of Squares | Mean Square | F-Value | P-Value |
|---|---|---|---|---|---|
| Treatment | 1 | .825 | .825 | 1.802 | .1945 |
| Residual | 20 | 9.161 | .458 | | |

Model II estimate of between component variance: .036

Fisher's PLSD for FU MLD
Effect: Treatment
Significance Level : 5 %
Inclusion criteria: Criteria 1 from      angio data

|  | Mean Diff. | Crit. Diff. | P-Value |
|---|---|---|---|
| Control, Cryo | -.403 | .626 | .1945 |

ANOVA Table for FU % DS
Inclusion criteria: Criteria 1 from      angio data

|  | DF | Sum of Squares | Mean Square | F-Value | P-Value |
|---|---|---|---|---|---|
| Treatment | 1 | 1603.955 | 1603.955 | 3.333 | .0829 |
| Residual | 20 | 9623.500 | 481.175 | | |

Model II estimate of between component variance: 110.273

Fisher's PLSD for FU % DS
Effect: Treatment
Significance Level 5 %
Inclusion criteria: Criteria 1 from      angio data

|  | Mean Diff. | Crit. Diff. | P- Value |
|---|---|---|---|
| Control, Cryo | 17.750 | 20.280 | .0829 |

FIG. 12C

CRYOGENICALLY ENHANCED INTRAVASCULAR INTERVENTIONS

CROSS-REFERENCE TO RELATED APPLICATIONS

The present application is a continuation application of U.S. patent application Ser. No. 09/511,191 filed on Feb. 23, 2000 now U.S. Pat. No. 6,468,297, which is a non-provisional of and claims the benefit of priority from U.S Provisional Patent Application Ser. No. 60/121,637 filed Feb. 24, 1999; and U.S. Provisional Patent Application Ser. No. 60/169,109 filed Dec. 6, 1999, the full disclosure of which are incorporated herein by reference.

BACKGROUND OF THE INVENTION

1. Field of the Invention

The present invention relates generally to apparatus and methods for treating atherosclerotic disease. In a particular embodiment, the present invention provides a combination of controlled cryogenic cooling and balloon distention of a diseased vessel wall.

A number of percutaneous intravascular procedures have been developed for treating atherosclerotic disease in a patient's vasculature. The most successful of these treatments is percutaneous transluminal angioplasty (PTA). PTA employs a catheter having an expansible distal end (usually in the form of an inflatable balloon) to dilate a stenotic region in the vasculature to restore adequate blood flow beyond the stenosis. Other procedures for opening stenotic regions include directional arthrectomy, rotational arthrectomy, laser angioplasty, stenting, and the like. While these procedures have gained wide acceptance (either alone or in combination, particularly PTA, in combination with stenting), they continue to suffer from significant disadvantages. A particularly common disadvantage with PTA and other known procedures for opening stenotic regions is the subsequent occurrence of restenosis:

Restenosis refers to the re-narrowing of an artery following an initially successful angioplasty or other primary treatment. Restenosis typically occurs within weeks or 30 months of the primary procedure, and may affect up to 50 % of all angioplasty patients to some extent. Restenosis results at least in part from smooth muscle cell proliferation in response to the injury caused by the primary treatment. This cell proliferation is referred to as "hyperplasia." Blood vessels in which significant restenosis occurs will typically require further treatment.

A number of strategies have been proposed to treat hyperplasia and reduce restenosis. Previously proposed strategies include prolonged balloon inflation, treatment of the blood vessel with a heated balloon, treatment of the blood vessel with radiation, the administration of anti-thrombotic drugs following the primary treatment, stenting of the region following the primary treatment, and the like. While these proposals have enjoyed varying levels of success, no one of these procedures is proven to be entirely successful in avoiding all occurrences of restenosis and hyperplasia.

It has recently been proposed to prevent or slow reclosure of a lesion following angioplasty by remodeling the lesion using a combination of dilation and cryogenic cooling. Co-pending U.S. patent application Ser. No. 09/203,011, filed Dec. 1, 1998, the full disclosure of which is incorporated herein by reference, describes an exemplary structure and method for inhibiting restenosis using a cryogenically cooled balloon. While these proposals appear promising, the described structures and methods for carrying out endovascular cryogenic cooling would benefit from still further refinements and improvements.

In light of the above, it would be desirable to provide improved devices, system, and methods for treatment of diseased blood vessels. It would be further desirable if these improved techniques were compatible with known methods for treating atherosclerotic disease, but reduced the actual occurrence and/or extent of restenosis due to hyperplasia. It would be particularly desirable if these improved techniques were capable of delivering treatment in a very safe and controlled manner so as to avoid injury to adjacent tissues. These devices, systems, and methods should ideally also inhibit hyperplasia and/or neoplasia in the target tissue with minimum side effects, and without requiring a complex control system or making a physician introduce numerous different treatment structures into the target area. At least some of these objections will be met by the invention described hereinafter.

2. Description of the Background Art

A cryoplasty device and method are described in WO 98/38934. Balloon catheters for intravascular cooling or heating of a patient are described in U.S. Pat. No. 5,486,208 and WO 91/05528. A cryosurgical probe with an inflatable bladder for performing intrauterine ablation is described in U.S. Pat. No. 5,501,681. Cryosurgical probes relying on Joule-Thomson cooling are described in U.S. Pat. Nos. 5,275,595; 5,190,539; 5,147,355; 5,078,713; and 3,901,241. Catheters with heated balloons for post-angioplasty and other treatments are described in U.S. Pat. Nos. 5,196,024; 5,191,883; 5,151,100; 5,106,360; 5,092,841; 5,041,089; 5,019,075; and 4,754,752. Cryogenic fluid sources are described in U.S. Pat. Nos. 5,644,502; 5,617,739; and 4,336, 691. The following U.S. Patents may also be relevant to the present invention: U.S. Pat. Nos. 5,458,612; 5,545,195; 5,733,280; 5,902,299; and 5,868,735. The full disclosures of each of the above U.S. patents are incorporated by reference.

SUMMARY OF THE INVENTION

The present invention provides new techniques for treating atherosclerotic disease using controlled cryogenic cooling. The invention may make use of a combination cryogenic/angioplasty catheter, eliminating any need for an exchange procedure to be preformed between dilation of a stenotic region within a vessel wall and the application of cryogenic cooling to inhibit hyperplasia. The cooling catheter may be suitable for cooling the diseased blood vessel before, during, and/or after dilation. Advantageously, controlled cooling of the vessel wall changes its mechanical properties so as to enhance the ease of concurrent and/or subsequent dilation. More specifically, the cooling process may weaken the vessel and allows it to be expanded with a much lower balloon pressure than with conventional uncooled angioplasty. Controlled cooling of the vessel wall has been found to effectively reduce actual and/or observed hyperplasia as compared to conventional uncooled treatment of the blood vessel. Reductions in restenosis may be provided for primary treatments of the blood vessel including angioplasty, directional arthrectomy, rotational arthrectomy, laser angioplasty, stenting, and the like. Cooling of the vessel wall will often be performed through plaque, and the cooling process will preferably take the thermodynamic effects of the plaque into account so as to enhance efficacy while inhibiting morbidity.

In a first aspect, the present invention provides a method for treating hyperplasia or neoplasia of a blood vessel region. The method comprises cooling an inner surface of the blood vessel region to a temperature and for a time sufficient to remodel the blood vessel such that observed subsequent excessive cell growth-induced stenosis of the blood vessel is reduced as compared to a stenosis of an equivalently treated uncooled blood vessel region.

Typically, the cooling will reduce stenosis by a relative amount of at least about 5% of the stenosis which would otherwise occur in the vessel, preferably by at least about 10%, and more preferably by at least about 25%. Ideally, the cooling step effects a relative reduction of the stenosis of at least about 50% of the equivalent vessel region stenosis, and may even be tailored to reduce stenosis by about 80% or more. Measured reductions in absolute stenosis percentages often measure more than 6%, preferably being more than 8%, and in experiments described herein, have been shown to be more than 15% and even better than 22%. Such benefits are provided by cooling times in a range from about 10 to about 30 seconds, and with the cooling temperature of the inner surface of the blood vessel being in a range from about 4° C. to about −31° C. (preferably being in a range from about −5° C. to about −15° C.).

In another aspect, the invention provides a method for inhibiting restenosis of a blood vessel region of a mammal. The blood vessel region is subjected to a primary treatment effecting an initial reduction in stenosis and inducing the restenosis. Typical primary treatments include directional angioplasty, arthrectomy, rotational arthrectomy, laser angioplasty, stenting, and the like. The method comprises cooling an inner surface of the blood vessel region to a temperature and for a time sufficient to remodel the blood vessel region such that observed restenosis of the blood vessel is measurably inhibited. Typically, the cooling step induces at least one of apoptosis, cell membrane damage, and programmed cell death so as to provide these advantages.

In another aspect, the invention provides a method for inhibiting restenosis of a blood vessel region. The blood vessel region is subjected to a primary treatment effecting an initial reduction in stenosis and inducing the restenosis. The method comprises cooling an inner surface of the blood vessel region, and then reducing cooling so that the inner surface of the blood vessel warms. The warmed inner surface is re-cooled so as to define at least one cooling/warming/cooling cycle. The at least one cycle has cooling temperatures and cooling times sufficient to remodel the blood vessel region such that the restenosis of the blood vessel is measurably inhibited.

In another aspect, the invention provides a method for treating a blood vessel. The blood vessel has plaque disposed between a lumen and a vessel wall of tissue. The method comprises cooling the vessel wall tissue to a temperature sufficient to inhibit excessive subsequent cell growth-induced stenosis of the blood vessel. This cooling step is performed by engaging a surface of the plaque with a cooling surface, and cooling the plaque with the cooling surface so that the plaque cools the vessel wall tissue.

Preferably, the vessel wall tissue will be cooled to a target temperature in the range from about −4° C. to about −15° C. It should be noted that the cooling surface will often cool the lesion to a temperature significantly below that of the target temperature, as a significant thermogradient may exist between an inner surface of the plaque and a plaque/endothelial tissue interface. In fact, the cooling surface may cool the plaque to a temperature below the −5° C. to −15° C. range.

In many embodiments, the vessel wall may be cooled to the target temperature for less than about 20 seconds, typically being cooled for at lest about 10 seconds. A rate of change of temperature of the vessel wall tissue may be significantly less than a rate of change of a plaque surface temperature, again in recognition of the thermodynamic effects of the plaque. Hence, in part because the presence of the plaque, the vessel wall tissue may stay at a reduced temperature for a significant amount of time after cooling is terminated. In general, at least one of the characteristics of the cooling process, such as a temperature of the cooling surface and/or a cooling time, may be determined at least in part based on a thickness of the plaque, as the plaque may have a surprisingly large impact on the cooling regimen to provide the desired tissue temperature cycle.

BRIEF DESCRIPTION OF THE DRAWINGS

FIGS. 7 and 7A illustrate an alternative cryogenic treatment catheter.

FIGS. 8A through 12C are graphical results of experiments showing an actual and observed reduction in restenosis and hyperplasia as described in the three Experimental sections provided hereinbelow.

DESCRIPTION OF THE SPECIFIC EMBODIMENTS

The devices, systems, and methods of the present invention are related to those of co-pending U.S. patent application Ser. No. 09/203,011, filed on Dec. 1, 1998 for an Apparatus and Method for Cryogenic Inhibition of Hyperplasia. That application is assigned to the present assignee, and its full disclosure is incorporated herein by reference.

Figure 1:
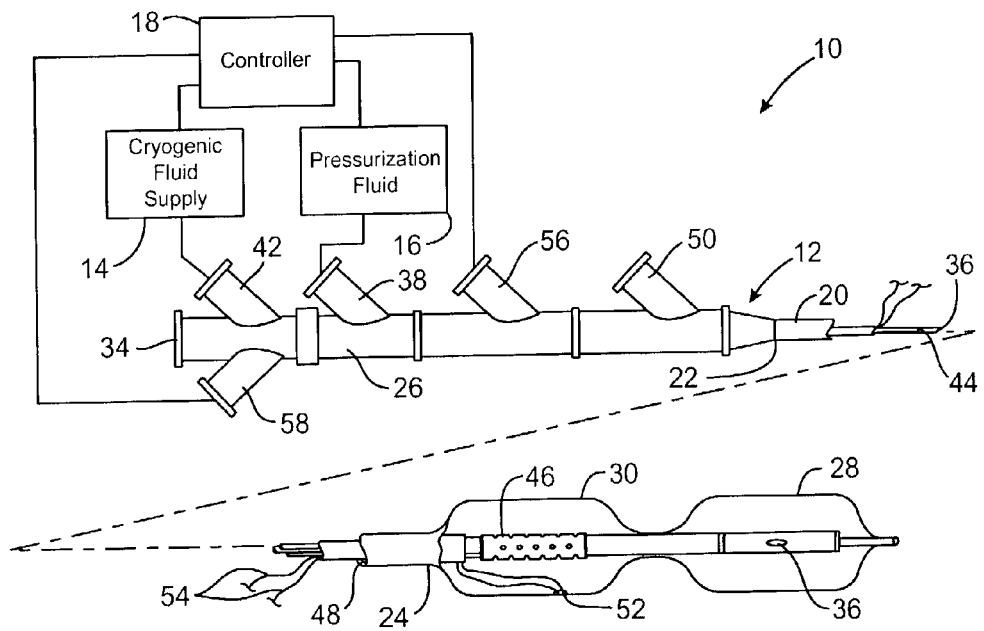
FIG. 1 schematically illustrates a combined cryogenic/angioplasty system including a catheter with an angioplasty balloon that is axially displaced from a cryogenic balloon.

Referring now to FIG. 1, an exemplary system 10 is capable of treating a diseased vessel wall of a blood vessel using a combination of both angioplasty dilation and cryogenic cooling. In general, system 10 includes a catheter 12 coupled to a cryogenic fluid supply system 14 and an angioplasty pressurization system 16. One or both of cryogenic system 14 and pressurization system 16 may be operatively coupled to a controller 18 for coordination of cooling and dilation, as will be described in more detail hereinbelow.

Catheter 12 generally includes a catheter body 20 having a proximal end 22 and a distal end 24. A proximal housing 26 includes a number of ports for coupling of cryogenic system 14, pressurization system 16, and the like to the proximal end of the catheter body. An angioplasty balloon 28 and a cryogenic balloon 30 are mounted near the distal end 24 of catheter body 20. The catheter body will generally be flexible and contain a plurality of lumens to provide fluid communication between the ports of proximal housing 26 and balloons 28 and 30.

Angioplasty balloon 28 may be formed from a variety of materials conventionally used for dilating blood vessels. Angioplasty balloon 28 will typically comprise a non-dispensable material such as polyethylene terephthalate (PET). Such angioplasty balloons are formed in a variety of sizes depending on their intended use, typically having a length in a range from about 15 mm to about 50 mm and an expanded diameter in a range from about 2 mm to about 10 mm. Prior to inflation, angioplasty balloon 28 will generally remain in a low profile configuration suitable for insertion into and maneuvering through the vascular system. A guidewire lumen 32 extends through angioplasty balloon 28 and cryogenic balloon 30 from a proximal guidewire port 34 to facilitate accessing the target treatment site.

Angioplasty balloon 28 is inflated by injecting fluid from pressurization system 16 into a pressurization lumen 36 through a pressurization port 38. In the embodiment of FIG. 1, balloon 28 will preferably be isolated from balloon 30, so as to avoid inadvertent inflation of the cryogenic balloon during dilation. High contrast markers may be provided within the balloon to enhance an image of the distal end of the catheter and facilitate positioning of the balloon fluoroscopically, sonographically, or under any other alternative image modality (with appropriate contrast structures). Such markers may be formed by winding a gold or platinum wire around the tubular structure defining pressurization lumen 36, as illustrated.

In the embodiment of FIG. 1, cryogenic balloon 30 is disposed proximally of angioplasty balloon 28. This arrangement is advantageous for first at least partially dilating the vessel wall and then treating the dilated vessel wall with cryogenic cooling, which can facilitate positioning of the cryogenic balloon within an occluded region of the vessel. In alternative embodiments, the cryogenic balloon may be disposed distally of the angioplasty balloon.

Figure 2:
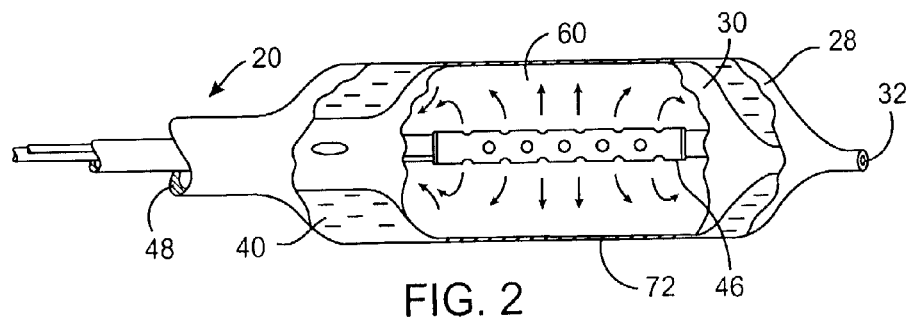
FIG. 2 illustrates an alternative distal end of the cryogenic/angioplasty catheter for use in the system of FIG. 1, in which a cryogenic balloon is nested within an angioplasty balloon.

The structure and operation of cryogenic balloon 30 may be understood with reference to FIGS. 1 and 2, and also with reference to U.S. patent application Ser. No. 09/203,011, previously incorporated herein by reference. Cryogenic fluid will often be injected into a cryogenic supply port 42 and passed toward cryogenic balloon 30 through cryogenic supply lumen 44 within catheter body 20. The cryogenic fluid may comprise cryogenic liquids or liquid/gas mixtures, optionally including carbon dioxide, nitrous oxide, liquid nitrogen, or the like. As the cryogenic liquid passes from supply lumen 44 and into cryogenic balloon 30, it is preferably distributed both radially and axially by a diffuser 46. Diffuser 46 will generally comprise a tubular structure with radially oriented openings. As the openings are radially oriented, diffuser 46 will direct the cooling fluid roughly perpendicularly against the wall of cryogenic balloon 30, so that the heat transfer coefficient between the cooling vapor and balloon wall is quite even and quite high. This helps to reduce the temperature of the balloon wall and provides greater heat extraction for a given flow rate of coolant into the balloon. Additionally, as the ports of diffuser 46 are distributed both circumferentially and axially along the balloon, the diffuser can provide a substantially uniform cooling over a significant portion of (often over the majority of) the surface of the balloon.

In some embodiments, the cryogenic cooling fluid may pass through a Joule-Thomson orifice between fluid supply lumen 44 and balloon 30. In other embodiments, at least a portion of the cryogenic cooling fluid may exit one or more ports into the balloon as a liquid. The liquid will vaporize within the balloon, and the enthalpy of vaporization can help cool the surrounding vessel wall. The liquid may coat at least a portion of the balloon wall so as to enhance even cooling over at least a portion of the vessel wall. Hence, the ports of diffuser 46 may have a total cross-section which is smaller than a cross-section of the fluid supply of lumen 44, or which is at least as large as (or larger than) the cross-section of the fluid supply lumen.

After the cryogenic cooling fluid vaporizes within balloon 30, it escapes the balloon proximally along an exhaust lumen 48 and is exhausted from catheter 12 through an exhaust port 50. Inflation of cryogenic balloon 30 may be controlled by the amount of cryogenic fluid injected into the balloon, and/or by the pressure head loss experience by the exhaust gases. Cooling is generally enhanced by minimizing the pressure within balloon 30. To take advantage of this effect so as to control the amount of cooling a fixed or variable orifice may be provided at exhaust port 50. Alternatively, a vacuum may be applied to the exhaust port to control cooling and enhance cooling efficiency.

An exemplary structure for diffuser 46 may comprise a polyimide tube having an inner diameter of about 0.032 inches and a wall thickness of 0.001 inch. Each port will define a diameter of about 0.0025 inches. There will typically be between six and six hundred ports in diffuser 46. In the exemplary embodiment, four axial rows of ports are separated by about 90° from each other. The rows are axially staggered so that the ports in a single row have central line separations of about 4 mm, while the ports of adjacent rows are separated by about 2 mm. The overall length of the porous diffuser tube will vary with the length of the balloon, and will typically be about 2 cm.

Diffuser 46 may be bonded concentrically about a central shaft defining guidewire lumen 32. Adhesives seal the proximal and distal ends of the diffuser, or the diffuser can be incorporated at the distal end of tube 64 with an adhesive seal at the distal end of the diffuser. High contrast markers may again be provided to enhance an image of the catheter and facilitate positioning of cryogenic balloon 18 at the treatment site. The cryogenic cooling fluid will generally be introduced through the annular space between the diffuser tube and the central shaft proximally of the balloon. The central shaft will typically comprise a polyimide tube, but may alternatively include any of a wide variety of materials.

In some embodiments, a temperature sensor may be thermally coupled to balloon 30 to monitor and/or control cryogenic cooling of the arterial wall. Temperature sensor 52 may optionally be disposed on an inner or outer surface of balloon 30, and is coupled to controller 18 by thermocouple leads 54. Temperature sensor 52 may comprise a thermocouple, thermistor, or the like.

To inhibit restenosis, controller 18 will generally initiate, monitor, and/or control cooling of the tissue. Cryogenic supply 14 will often inject sufficient cryogenic cooling fluid to effect a cooling rate of the tissue in a range from about 2°

C. to about 30° C. per second. In an exemplary treatment, the system will maintain the temperature in a range from about 0° C. to about −80° C., optionally at a temperature in range from −5° C. to about −40° C., for a time between about 1 and 60 seconds, ideally maintaining the tissue at a temperature in a range from about −5° C. to about −15° C. for a time from about 10 to about 20 seconds. The efficacy of the therapy at inhibiting restenosis may be enhanced by repeatedly cooling the tissue to such temperatures for between 1 and 5 cooling cycles, typically repeating between 1 and 6 cooling cycles every 60 seconds. Typical treatment cycles may cool a surface temperature of the endothelium down to about −10° C., then allow the surface temperature to warm to about 0° C. Five of these cooling cycles might be performed in about 40 seconds. To provide cooling, a cryogenic liquid or liquid/gas mixture comprising carbon dioxide, nitrous oxide, or the like may flow through the balloon at a rate in an average from about 100 to about 800 mg per second. Such cooling (and optional cooling cycles) may induce apoptosis and/or programmed cell death.

To accurately control and/or monitor the pressure within cryogenic balloon 30, proximal housing 26 may include a cooling balloon pressure monitoring port 56. The pressure monitoring port will be in fluid communication with the cryogenic balloon 30, preferably through a dedicated pressure monitoring lumen (not shown). Signals from pressure monitoring port 56 and a thermal couple connector 58 may be transmitted to the controller 18. This allows the use of a feedback control system for initiating, regulating, and halting the supply of cryogenic fluid from fluid supply system 14. More specifically, the controller will often provide a control signal to the fluid supply system in response to signals from pressure monitoring port 56 and/or thermocouple connector 58.

Referring now to FIG. 2, an alternative combination cryogenic/angioplasty catheter again includes both a cryogenic balloon 30 and an angioplasty balloon 28. In this embodiment, cryogenic balloon 30 is nested within angioplasty balloon 28, so that if the low pressure cooling balloon were to break during the procedure, the higher pressure capability of the surrounding angioplasty balloon 28 would contain the exhaust gases until the flow of coolant was stopped. In other respects, the structure of this nested embodiment is quite similar to that described above.

In use, the nested cryogenic/angioplasty balloon catheter of FIG. 2 may allow pre-cooling of a diseased vessel wall prior to dilation, cooling of a vessel wall after dilation, interspersed cooling/dilation, and even concurrent dilation during cooling. Advantageously, the catheter need not be repositioned between the application of dilation pressure and cryogenic cooling. Hence, this nested embodiment facilitates the immediate sequential pre- and/or post-cooling of the stented vessel wall, thereby giving a wide flexibility in the treatment protocol. Advantageously, the interaction of cooling and dilation may be precisely prescribed and effected by controller 18 (see FIG. 1) without having to wait for the surgeon to reposition the catheter.

Where the vessel wall is to be at least partially dilated prior to cryogenic cooling, angioplasty balloon 28 may be inflated first with contrast liquid 40 (as used in conventional angioplasty). The contrast liquid may then be at least partially evacuated, allowing cooling balloon 30 to be inflated at a pressure that is lower than the angioplasty distention pressure. Inflation of cryogenic balloon 30 pushes the angioplasty balloon against the diseased wall of the vessel, so that the cryogenic fluid 60 within the cryogenic balloon is thermally coupled to the diseased vessel wall by both the cryogenic balloon wall and the angioplasty balloon wall in series. To enhance heat flow through the balloon walls, a heat transfer enhancing material may be included in cryogenic balloon 30 and/or angioplasty balloon 28, particularly where treatment temperatures of about −50° C. and below are desired. For example, the addition of between about 1% and 10% boron nitride in a polyethylene or other balloon polymer can significantly improve heat transfer of the entire system. Surprisingly, a significant temperature differential may be found between an inner and outer surface of each balloon during cooling. Hence, improving the thermal conductivity of each balloon wall disposed between cryogenic fluid 60 and the targeted wall of the vessel may provide significant benefits when cooling to low temperatures.

In alternative methods for using the nested cryogenic/angioplasty balloon of FIG. 2, cooling may be initiated prior to complete dilation of the stented region of the vessel. The cooling process may weaken the mechanical properties of the vessel and allow it to be expanded or dilated at a much lower pressure than is used with conventional angioplasty. For example, dilation of a cryogenically cooled vessel may require inflation of angioplasty balloon 28 with a fluid pressure of about 2 bar, as compared to about 10 bar for conventional uncooled angioplasty on the same vessel wall. Simultaneous cryogenic cooling and angioplasty may reduce and/or eliminate medial vessel fractures, thereby inhibiting proliferative response after angioplasty. It should be noted that at least some of these advantages may be provided by using a single balloon coupled to both a cryogenic supply system 14 and a pressurization system 16. Such a cooling/angioplasty catheter used in this fashion may allow the operator to perform both angioplasty and cryogenic antiproliferative treatments with a single inflation cycle of the balloon.

Still further alternative treatment cycles are possible, including inflating a balloon with a room temperature gas at normal angioplasty pressures to dilate the vessel, and then inflating the balloon with a cryogenic fluid or other coolant to treat the dilated area so as to inhibit hyperplasia. Alternatively, a balloon may be inflated with a standard angioplasty contrast liquid at normal angioplasty pressures to dilate the vessel. The balloon may then be flushed with saline, and then flushed with a dry room temperature gas to dry the cooling fluid path. After the cryogenic fluid path is dry, the balloon may be inflated with a coolant to treat the dilated area. Cooling cycles before angioplasty and/or before stenting may also provide the antiproliferative response described above.

Figure 3:
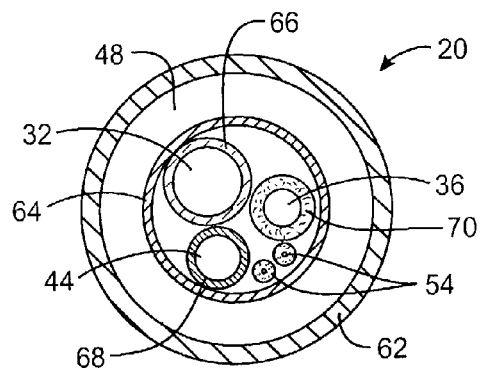
FIG. 3 is a cross-section taken along the catheter body of the cryogenic/angioplasty system of FIG. 1.

Referring now to FIG. 3, the structure of catheter body 20 is illustrated in cross-section. An outer sheath 62 partially defines exhaust lumen 48, the exhaust lumen here comprising an annular space disposed between the sheath and an inner jacket 64. In, the exemplary embodiment, sheath 62 comprises a polyethylene tube having an inner diameter of 0.058 inches and a wall thickness of about 0.003 inches. The exemplary jacket 64 comprises a polyimide having an inner diameter of 0.035 inches and a wall thickness of 0.001 inches.

Within jacket 64, a core shaft 66 defines guidewire lumen 32, while a cooling inlet tube 68 and an angioplasty pressurization tube 70 define supply lumen 44 and pressurization lumen 36, respectively. The exemplary cooling inlet tube comprises a polyester or polyimide, while the pressurization tube in the exemplary system may comprise a polyester or high density polyester. A wide variety of alternative materials might also be used. Thermocouple leads 54 are insulated in a conventional manner.

Figures 4A, 4B:
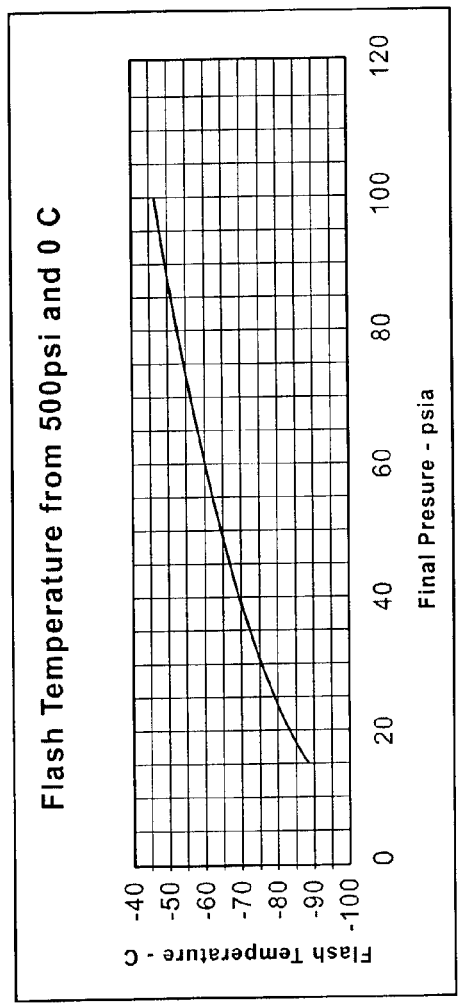
FIGS. 4A and 4B illustrate cryogenic cooling temperatures provided by expansion of $N_2O$.

The above discussion describes structures and techniques for enhancing the efficiency of cryogenic cooling within a blood vessel. However, cryogenic cooling is capable of inducing temperatures well below the preferred antiproliferative treatment ranges of the present invention (typically in a range from about −5° C. to about −15° C.). Referring now to FIGS. 4A and B, expansion of N20 from an initial pressure of 500 psi and an initial temperature of 0° C. to final pressures in a range from atmospheric pressure to 100 psi results in a cryogenic cooling fluid temperature significantly colder than our preferred target tissue temperatures. As it may be convenient to make use of commercially available 500 psi N20, it may be beneficial to include an additional temperature control mechanism to provide our desired treatment temperatures. While it may be possible to maintain expanded cryogenic fluid pressures above 100 psi, the use of such high pressure gases within the vasculature may involve a significant risk of serious injury if the high pressure gases escape the catheter and enter the blood stream.

Referring once again to FIG. 2, one simple technique for reducing tissue cooling without increasing fluid within our balloon structures is to add a layer of insulating material 72 between the cryogenic cooling fluid and the tissue engaging surface of the balloon. A suitable insulation material might include a thin layer of expanded Teflon™ (ePTFE) on an inner or outer surface of cryogenic balloon 30, on an inner or outer surface of angioplasty balloon 28, or the like. The ePTFE layer may have a thickness in the range from about 0.00025 inches to about 0.001 inches. A wide variety of alternative insulation materials might also be used. Alternative active temperature control techniques might be used with or without such an insulation layer, including the use of controller 18 as shown in FIG. 1.

Figure 5:
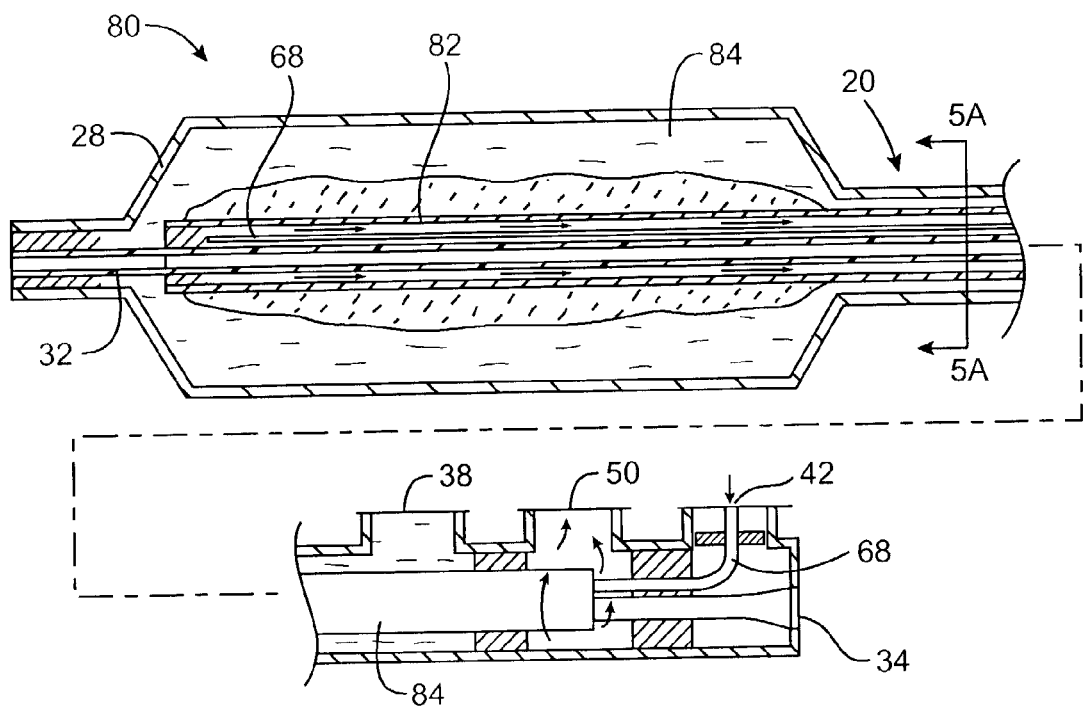
FIGS. 5 and 5A illustrate a particularly preferred controlled temperature cryogenic catheter in which a saline solution having a predetermined freezing temperature controls the cooling of tissues by thermally coupling an inexpansible heat exchanger with a surrounding angioplasty balloon.
Figure 5A:
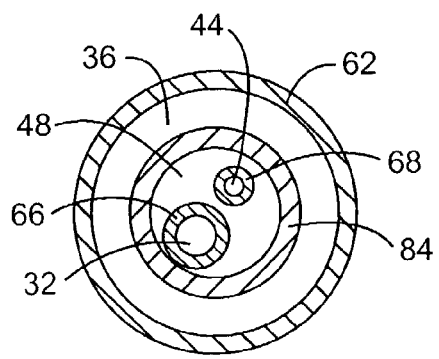

A particularly advantageous temperature control mechanism can be understood with reference to FIGS. 5 and 5A. In this embodiment, a controlled temperature cryogenic balloon catheter 80 again includes an angioplasty balloon 28, which here contains an inexpansible heat exchanger 82. Cooling of fluid inlet tube 68 releases the cryogenic cooling fluid within heat exchanger 82, but does not expand the heat exchanger into direct thermal contact with the balloon wall of angioplasty balloon 28. Instead, a saline solution 84 thermally couples the heat exchanger to the outer surface of angioplasty balloon 28.

Saline solution 84 will generally have a predetermined freezing temperature, and sufficient cryogenic cooling fluid will generally be provided to heat exchanger 82 so that the saline solution is only partially frozen. As a result, the temperature of the saline solution within angioplasty balloon 28 will be maintained accurately at the freezing temperature. As the freezing temperature of saline may be varied by changing the salinity, this provides a convenient control mechanism to vary the treatment temperature. Specifically, a 6% saline solution will freeze at about −3.5° C., while an 18% saline solution will freeze at about −14° C. By varying the salinity between about 6% and 18%, the temperature of the saline solution during cryogenic cooling (while the saline is partially frozen) can be selected within a range from about 5° C. to about 15° C. In an exemplary embodiment, a 12% saline solution will provide a freezing temperature of about 8° C., which is particularly advantageous for use with the controlled-temperature cryogenic catheter 80 illustrated in FIG. 5.

It should be understood that there may be a significant temperature difference between the freezing temperature of saline solution 84 and the surface temperature of the endothelium, and that this variation may depend on the particular angioplasty balloon structure used. Nonetheless, these controlled temperature cryogenic catheters can take advantage of the latent heat of freezing to provide an accurate treatment temperature despite minor variations in the cryogenic cooling flow, exhaust gas pressure due to bending of the catheter shaft, or the like.

It should be understood that a variety of fluids, and possibly even solids, might be used in place of saline solution 84. In general, temperature control will be provided where a thermally coupling structure undergoes a change in phase involving a significant latent phase change energy. Nonetheless, saline is particularly preferred as its range of freezing temperatures can be easily controlled within the desired range, and as it poses little risk in the event of release within the vasculature. Optionally, contrast may be included with the saline solution to improve imaging of the system within the patient body.

In the exemplary embodiment illustrated in FIGS. 5 and 5A, heat exchanger 82 extends proximally from angioplasty balloon 28 to at least in part define exhaust lumen 48. This simple proximal tubular structure (which is referred to herein as an evaporator 84) may comprise a polyimide tube having an inner diameter in a range from about 0.036 inches to about 0.051 inches, ideally having an inner diameter of about 0.045 inches. Cooling inlet tube 68 within evaporator 84 and heat exchanger 82 may comprise a polyimide tube having an inner diameter in a range from about 0.005 inches to about 0.012 inches, ideally having an inner diameter of about 0.009 inches.

It is possible that evaporator 84 extending the entire length of the catheter may cause sufficient cooling of the saline proximally of the angioplasty balloon to induce freezing along catheter body 20. To reduce this, an insulation jacket may be provided around the evaporator proximally of heat exchanger 82. The insulation jacket may comprise a polyimide tube, preferably leaving a gap (as small as 0.001 inches) between the insulation jacket wall and evaporator 84. Alternatively, the balloon inflation lumen may be altered to prevent the saline from thermally coupling exhaust lumen 48 to outer sheath 64. For example, a polyimide tube having an inner diameter in a range from about 0.012 inches to about 0.025 inches may be disposed between evaporator 84 and outer sheath 62, with this additional tubular structure providing fluid communication between inflation port 38 and angioplasty balloon 28. In either of these embodiments, an additional port may be provided on the proximal housing in communication with the insulation gap (either between the insulation jacket and evaporator 84 or between evaporator 84 and outer sheath 62) such that at least some of the air could be evacuated from this gap to reduce heat transfer to in the blood surrounding catheter body 20 and the exhaust gases.

Figure 6A:
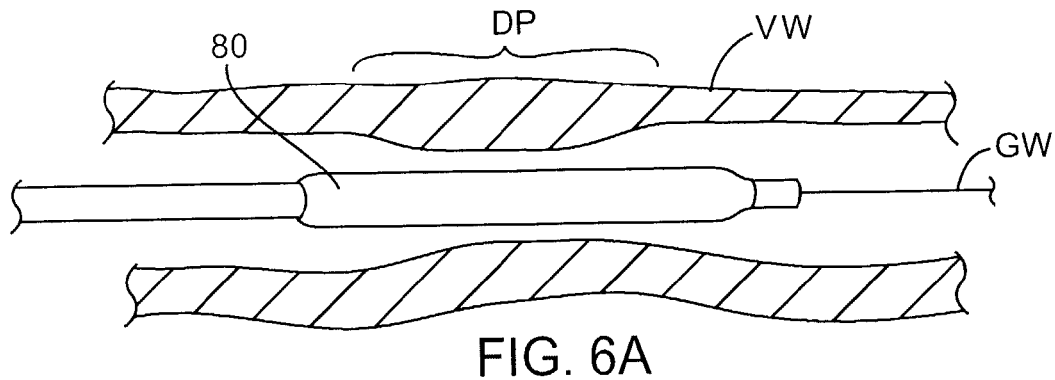
FIGS. 6A through 6C schematically illustrate a method for using the controlled temperature cryogenic balloon of FIG. 5.
Figure 6B:
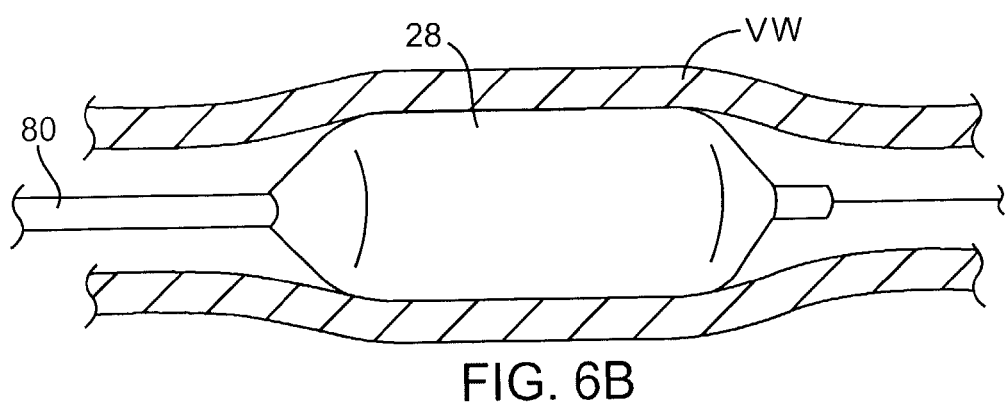
Figure 6C:
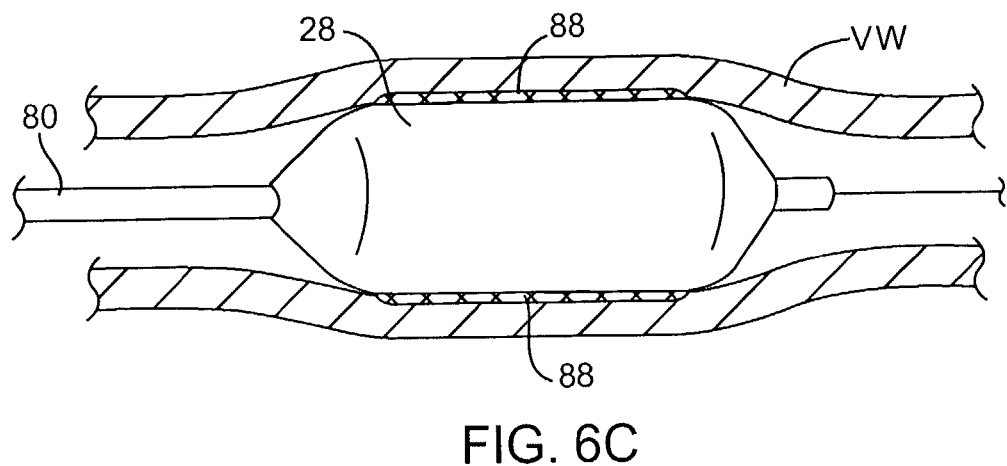

A method for using controlled-temperature cryogenic catheter 80 is illustrated in FIG. 6A through C. Typically, the catheter is introduced into the vasculature through an introducer sheath, most often using the widely known Seldinger technique. A guide wire GW is maneuvered through the vessel, and catheter 80 is advanced over the guide wire and positioned adjacent diseased portion DP of vessel wall VW.

Once angioplasty balloon 28 is in position, the balloon may be inflated in a conventional manner through inflation port 38 to dilate the vessel, as illustrated in FIG. 6B. Optionally, the vessel may be dilated using conventional contrast fluid to facilitate fluoroscopically directing dilation. When standard contrast has been used for dilation, the balloon may be evacuated and filled with a saline solution which freezes at the desired treatment temperature. Alternatively, dilation may be performed using this saline solution to avoid any delay between dilation and cryogenic treatment. In still further alternative treatments, cryogenic cooling may be initiated prior to or during dilation. Regardless, prior to cooling the saline solution having the predetermined freezing temperature will preferably be used to inflate angioplasty balloon 28 with sufficient pressure to provide good contact between the balloon and vessel wall VW. Typically, the angioplasty balloon will be inflated by the saline solution to a pressure in a range from about 5 psi to about 30 psi, as illustrated in FIG. 6B.

To initiate cooling, a cryogenic fluid (usually in the form of a liquefied refrigerant or liquid/gas mixture) is injected into cryogenic supply port 42. The cryogenic fluid flows through fluid supply lumen 44 and is transmitted into heat exchanger 82, where it rapidly absorbs heat and vaporizes, thereby cooling saline 84 and angioplasty balloon 28. As the coolant vaporizes, it passes proximally along evaporator 84 to exhaust port 50. Sufficient cryogenic cooling fluid is supplied to partially freeze saline 84, so that the saline liquid/solid mixture remains at about freezing temperature. Optionally, additional cryogenic cooling fluid may be introduced, with the freezing of the saline providing a temporary plateau along the temperature excursion profile. More typically, the partially frozen saline melts by absorbing heat from the surrounding body. In the meantime, the cooling of saline within angioplasty balloon 28 results in treatment of a surface layer 88 of vessel wall VW engaged by the angioplasty balloon to an accurately controlled treatment temperature in a range from about $-5°$ C. to about $-15°$ C. As a result, this treated tissue layer undergoes apoptosis, thereby avoiding and/or reducing the proliferative response of the luminal wall to dilation.

Figure 6D:
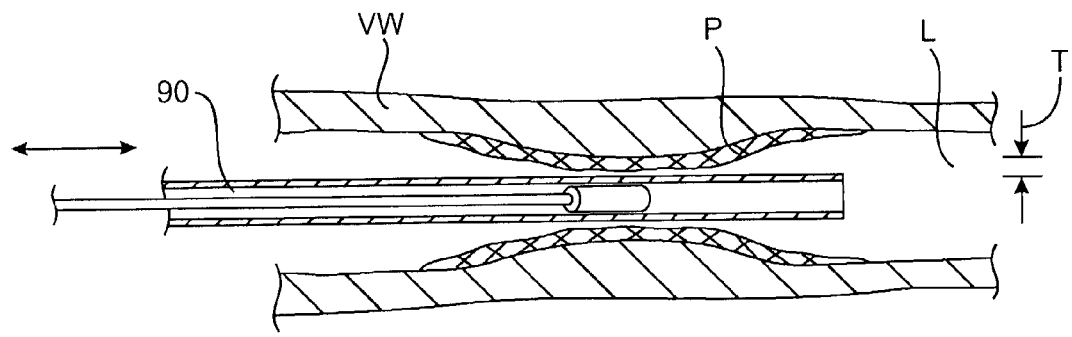
FIGS. 6D and 6E are partial cross-sections schematically illustrating methods for selectively cooling a tissue of the vessel wall to a desired temperature through a lesion along the vessel lumen such as plaque.
Figure 6E:
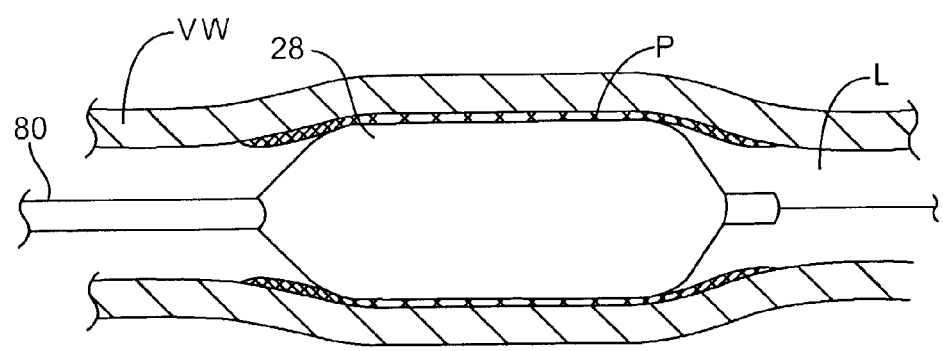
Figure 8A:
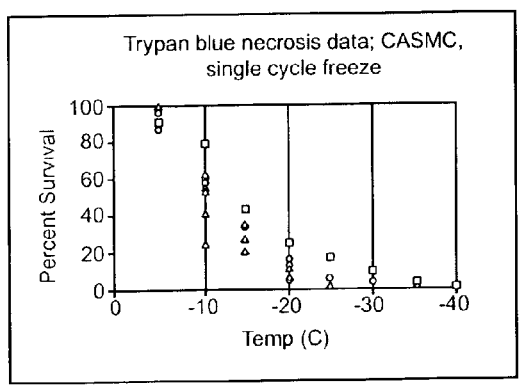
Figure 8B:
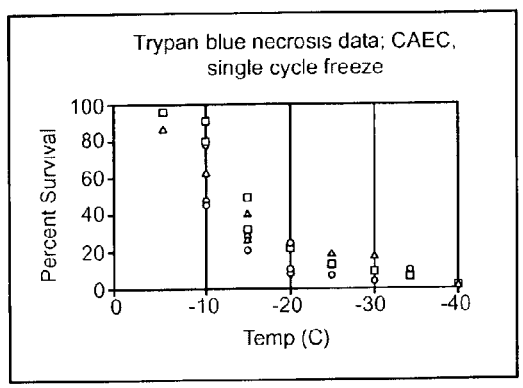
Figure 8C:
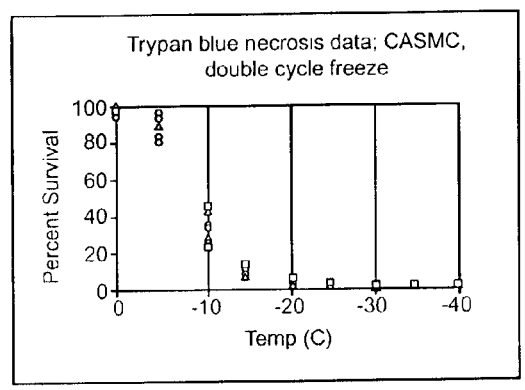
Figure 8D:
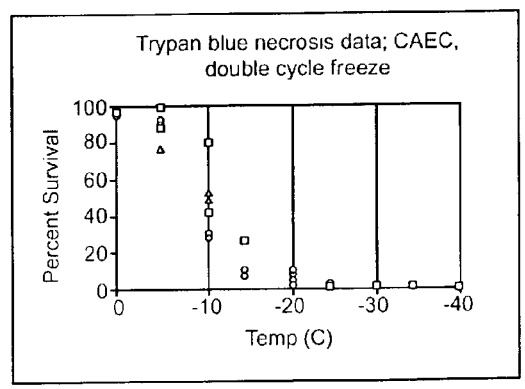
Figure 9A:
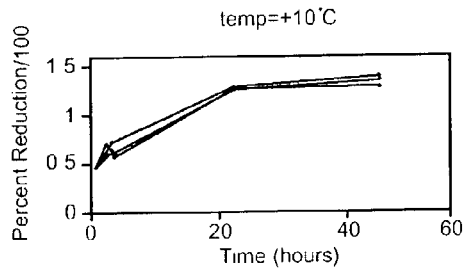
Figure 9B:
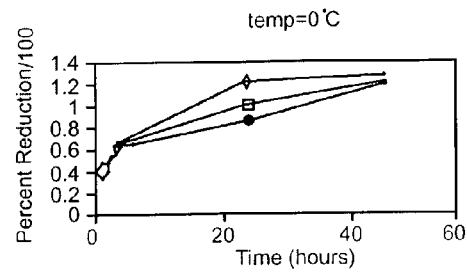
Figure 9C:
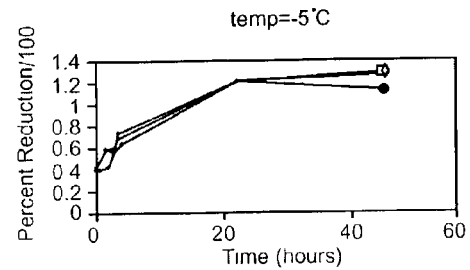
Figure 9D:
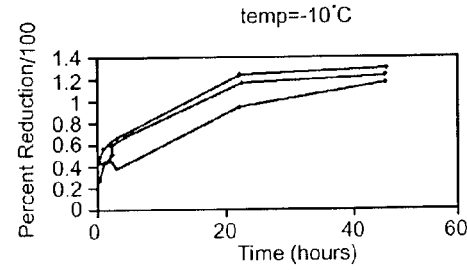
Figure 9E:
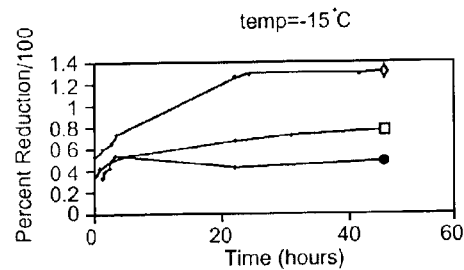
Figure 9F:
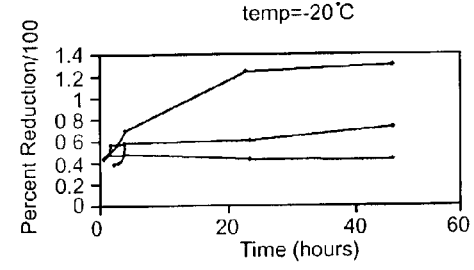
Figure 9G:
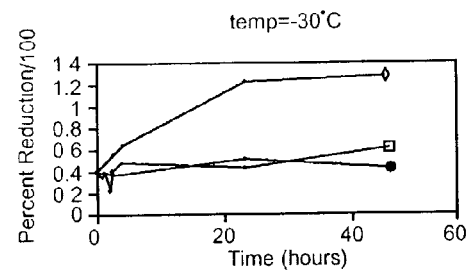
Figure 9H:
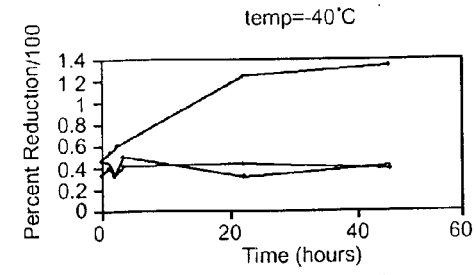
Figure 10A:
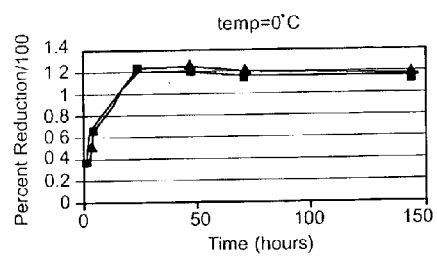
Figure 10B:
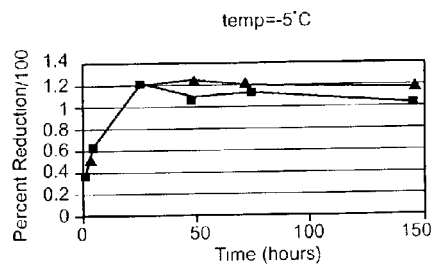
Figure 10C:
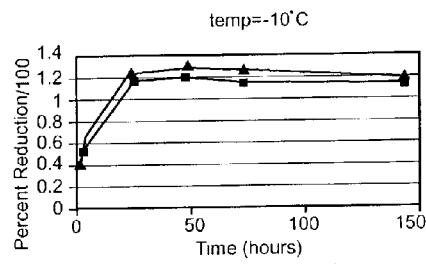
Figure 10D:
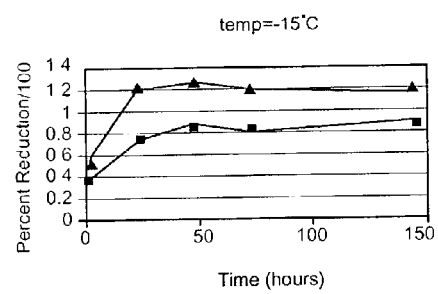
Figure 10E:
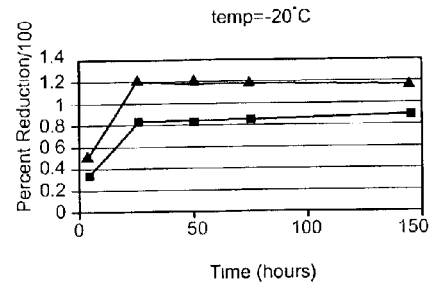
Figure 10F:
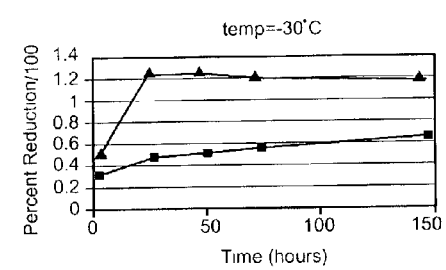
Figure 10G:
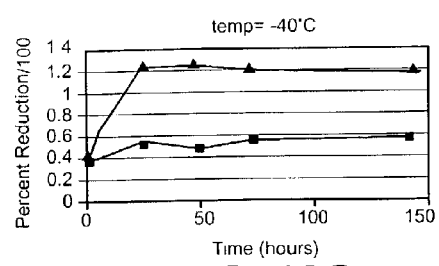

As can be understood from the device descriptions provided above, proper design of a cooling catheter can help to provide accurate treatment temperatures in a range from about $-5°$ C. to about $-15°$ C. In many embodiments, it will be desirable to maintain the target tissue within this range for a time between about 20 to about 60 seconds. As described in detail in the Experimental sections hereinbelow, accurately providing such treatment temperatures and times for treatment of the tissue can result in apoptosis without excessive immediate necrosis of the tissues of the vessel wall. Referring now to FIGS. 6D and 6E, many vessels targeted for a primary treatment such as angioplasty, stenting, atherectomy, and the like, may have a significant amount of plaque P disposed between a tissue of the vessel wall VW and the vessel lumen L. Plaque P can have a surprisingly large thermodynamic effect on the treatment of the tissues of vessel wall VW, as a significant temperature gradient may exist between a surface of the plaque adjacent lumen L and a plaque/vessel wall interface. Hence, providing a cooling surface such as a cooled balloon 28 (or optionally, a cooled liquid surface, or the like) engaging an inner surface of plaque P at a target temperature for cryotherapy may not reduce the temperature of the vessel wall tissue sufficiently to inhibit hyperplasia. Similarly, if the tissue of vessel wall VW is cooled accurately down to the desired treatment temperature, and if cooling is then maintained for the desired treatment time, the insulating effect of the plaque may maintain the vessel wall tissue at a reduced temperature for a significantly excessive amount of time.

To properly accommodate the conditions within a particular patient P, a thickness T of plaque P may be measured using an intravascular ultrasound system 90 as schematically illustrated in FIG. 6D. An exemplary ultrasound system is commercially available from Scimed of Maple Grove, Minn. Alternative methods for measuring plaque and other lesions within a lumen of a vessel include angiography, computer tomography, and a variety of other known medical sensing modalities.

Once thickness T of plaque P has been measured, a treatment time and/or temperature for cooling an outer surface of balloon 28 can be determined. Treatment times and/or temperatures may be calculated using a mathematical model which accounts for the insulating effect of plaque P. Alternative methods for determining treatment parameters may be based on dosimetry (based on prior measured treatments), or the like. Treatment parameters for maintaining cooling using balloon 28 may be adjusted for a thickness, thermal conductivity, or other characteristic of plaque P. For example, it may take approximately 10 seconds to cool the tissue of vessel wall VW to a treatment temperature in a range from about $-5°$ C. to about $-15°$ C. due in part to the presence of plaque P. Additionally, natural warming of the tissues of vessel wall VW may be inhibited after active cooling of balloon 28 has ceased due to the insulating effects of plaque P. In fact, active cooling for a time in a range from about 10 seconds to about 20 seconds after the vessel wall VW reaches the treatment temperature may be preferred, as the vessel wall tissue can remain at or near the treatment temperature due to the insulated, gradual cooling of the tissue. Even with this abbreviated active cooling of the balloon, the total cooling treatment may be comparable to a treatment in which active cooling of a balloon in direct contact with the vessel wall tissue is maintained for a time and a range from about 20 to about 60 seconds after temperatures reach a target temperature between about $-5°$ C. and about $-15°$ C.

In the following Experimental sections, treatment temperatures and times are generally given for tissue in substantially direct contact with the cooling surface. Where significant amount of plaque is present within a lumen of the vessel wall, the thermodynamic effects of that plaque will preferably be taken into account in the treatment cycle of the cryotherapy device so as to effect the described tissue treatments.

Experimental I

In Vitro Studies of Arterial Freezing Injury

Abstract

Objective: To investigate the effects of hypothermia and freezing on human arteries at the cellular level.

Methods: Cultured arterial endothelial cells and smooth muscle cells are chilled or frozen under controlled thermal conditions. Consequences such as necrosis or apoptosis, as well as the impact on long term reproductive viability are measured with a variety of assays.

Results: These data establish correlations between thermal conditions and the extent and nature of arterial freezing injury.

Introduction

The paradoxical ability of freezing to produce either preservation or destruction of biological tissues is well documented by researchers in cryobiology. The impact of cold exposure on biological systems is determined by precise thermal conditions such as final temperature, cooling and warming rates, and exposure dine, as well as biophysical parameters specific to each tissue type. In order to design a cryotreatment which will effectively assist in the prevention of arterial restenosis it is desirable to understand the specific relationships between thermal conditions and the degree and mechanisms of arterial freezing injury. With this objective, the following describes in vitro studies of the effect of chilling and freezing on two major arterial constituents; endothelial cells and smooth muscle cells.

Materials and Methods

Materials: Human coronary artery endothelial cells (CAEC) and smooth muscle cells (CASMC) obtained from Clonetics, are cultured in basal media supplemented with 5% fetal bovine serum and Clonetics supplied growth factors, and grown in a 37° C., humidified, 5% $CO_2$ environment. Freezing or chilling of cellular suspensions is carried out using a low temperature stage, which consists of a copper block machined to allow the circulation of liquid nitrogen through the block. A thermocouple mounted to the stage provides feedback to a temperature controller. This controller regulates the power input to a thermoelectric heater fixed to the copper block, thereby holding the temperature of the stage to within 1 degree Celsius of the desired, preset temperature.

Methods: Necrosis experiments: A 30 µl aliquot of cellular suspension stained with trypan blue is pipetted onto a precooled glass microslide positioned on the freezing stage, and immediately covered with a cover slip. After the allotted exposure time, the microslide is transferred to a 37° C. surface to thaw. For a second freezing cycle, the slide is moved back to the cold stage for the desired period of time, and then thawed on the 37° C. surface. Trypan blue is excluded by intact plasma membranes, so a count of stained vs. unstained cells immediately following the freezing treatment provides a measure of acute necrosis as reflected by membrane integrity, in these experiments, cells are subjected to final freezing temperatures ranging from +10 to –40° C. for 10, 20, and 60 second exposure times, and both single and double freeze/thaw cycles are considered.

Reproductive survival experiments: For each freezing condition, a 125 µl aliquot of cellular suspension is placed in the well of a sterile, precooled chamber slide on the low temperature stage. The chamber slide is transferred to a 37° C. surface to thaw the suspension, and then moved back onto the freezing stage if a second freeze/thaw cycle is desired. After thawing, the sample is transferred to a culture flask in a sterile field at a seeding density of $1 \times 10^4$ cells/$cm^2$, and incubated with growth medium mixed with 10% alamar blue. Alamar blue is an oxidation-reduction indicator, which yields a colorimetric change in response to metabolic activity. Using a plate reader, the reduction of the dye is monitored hourly for 4 hours after the freeze, and then at 24 hour intervals for up to 6 days. Reduction of the dye provides a quantitative measure of the proliferation of the treated cells. Again, a temperature range of +10 to –40° C. is examined, and single and double freeze/thaw cycles are used with 60 second cold exposure times.

Apoptosis experiments: Freezing experiments are carried out with both cellular suspensions and adherent cells. Cellular suspensions are frozen on chamber slides on the low temperature stage as described above. Adherent cells are frozen or chilled by immersion of the culture flasks in saline-ice baths which maintain the desired temperatures. After the allotted exposure time, the flasks are transferred to a 37° C. bath for 1 to 2 hours. The cells are removed from the flasks by trypsinization, and the cellular DNA is extracted using a lysing kit purchased from Boehringer-Mannheim. After elimination of RNA by incubation of the samples in RNase, the purified DNA is electrophoresed in a 1% agarose gel for 2.5 hours at 75 V. DNA is visualized with ethidium bromide using a UV transilluminator. DNA fragmentation indicative of apoptosis is detected by separation of the DNA into a characteristic ladder. In these studies, cell suspensions are exposed to final temperatures in the range of +5° to –15° C. for 60 seconds and undergo 1 to 4 freeze/thaw sequences. Adherent cells are cooled for longer periods of time, experiencing temperatures of +5 to –15° C. for 0.5, 1, 2, and 4 hours. Post freeze incubation times of 1 to 2 hours at 37° C. are enforced to allow apoptosis to progress to the DNA fragmentation stage. To determine how the occurrence of cold shock apoptosis is dependent on the cell growth phase, 24, 48, 72, and 120 hour cultures are used.

Results and Discussion

Necrosis experiments: The plots in FIGS. 8A through 8D present necrosis data obtained with trypan blue. These plots include data for cells exposed to final freezing temperatures for 60 seconds (circles), 20 seconds (triangles), and 10 seconds, (squares). From these plots it is evident that cells suffer no acute membrane damage when chilled or frozen to temperature above –5° C., and a substantial percentage of cells survive freezing to temperatures as low as –15° C. A double freeze/thaw cycle increases cellular damage, however in the higher temperature range from +10 to –5° C. the majority of cells still survive. The duration of cold exposure appears to have no effect on cell survival for the range of times considered in this study.

Reproductive survival experiments: The alamar blue reduction curves shown in FIGS. 9A through 9H and FIGS. 10A through 10G, give a measure of the number of metabolically active cells in each treated culture, relative to a sham operated control. In FIGS. 9A through 9H, the percent reductions of alamar blue in CASMC cultures are plotted as a function of time for sham operated control cells (diamonds), cells exposed to a single freeze cycle (squares), and cells exposed to a double freeze cycle (circles). In FIGS. 10A through 10G, percent reduction of alamar blue are plotted for CAEC cultures as a function of time for sham operated control cells (diamonds), and for cells exposed to a single freeze cycle (squares). From these plots it is evident that the growth of cells exposed to temperatures in the range from +10 to –10° C. is nearly equivalent to the growth of untreated cells, for both single and double freeze/thaw cycles over the course of 2–6 days following a cold treatment. At temperatures of –15 to –20° C. the growth of frozen cells is less than that of control cells, although some growth is still detected. At lower temperatures virtually no growth is found, and the cells are presumably 100% necrotic.

Apoptosis experiments: For the thermal conditions listed in the methods section, significant levels of cold shock induced apoptosis have not been detected. Since the electrophoresis assay requires a minimum fraction of cells to be undergoing apoptotic DNA fragmentation for the characteristic DNA ladder to become visible, it is possible that apoptotic events are occurring, but at a level too low to measure by this assay. More sensitive assays such as the TUNEL method will be used to quantify the effect of cold on cells in the higher non-necrotic temperature range, as described below.

Apoptosis

As discussed above, the goal of this study is to investigate the effects of cold exposure on human arteries at the cellular level. A study of freeze induced necrosis has been described above. However, freezing injury may manifest itself in forms other than acute cellular necrosis. An important mechanism of cellular death is apoptosis or "programmed cell death", which is characterized by internucleosomal cleavage of DNA, cell membrane blebbing, condensation of nuclear chromatin, and the fragmentation of the cell into smaller apoptotic bodies.

Cold shock can induce apoptosis. In particular, apoptosis can be triggered by exposure to temperatures ranging from 0 to −15° C., conditions which yield low levels of cellular necrosis. On this basis, studies were conducted to identify the role of apoptosis in the overall response to cold temperatures for the cells in this particular system. Apoptosis is especially interesting for this application because, unlike cellular necrosis, it does not cause the inflammation which marks the initiation of neointimal hyperplasia. The studies described in this section seek to assess whether the smooth muscle cells involved in the proliferative process of neointimal hyperplasia can be destroyed by inducing apoptosis rather than necrosis, thereby avoiding an inflammatory response. Because of the complexity of the apoptotic mechanisms, three assays have been applied to study the occurrence of cold shock apoptosis: gel electrophoresis, a TUNEL assay, and an Annexin V assay.

Experiments conducted with the gel electrophoresis assay were described above. As reported there, significant levels of cold shock induced apoptosis were not detected with the electrophoresis assay. However, this result does not necessarily rule out the presence of apoptosis. The gel electrophoresis assay has certain limitations. For instance, the appearance of the characteristic ladder pattern is dependent on the presence of a minimum quantity of fragmented DNA, making the detection of a positive result dependent of the number of cells in the sample population and the efficacy of the DNA isolation process, as well as the percentage of cells in the appropriate stage of the apoptotic process. Therefore, it is possible that apoptotic events took place, but at a level too low to measure by this assay. In addition to this, fragmentation of the DNA into characteristic lengths represents a specific stage in the apoptotic process. As that process continues, DNA fragments further and is sequestered in the smaller apoptotic bodies which are entirely digested by neighboring cells, so that the characteristic ladder is no longer produced. Thus, if the assay is applied to a cell population too early (before fragmentation begins) or too late in the apoptotic process, it will fail to identify apoptosis. The time taken for a particular cell type to undergo each step of the apoptotic process in response to a particular driving mechanism is unknown and can vary from minutes to hours. It is possible that significant levels of apoptosis were present in the treated samples, but the cells were not lysed at the critical moment in the process. For this reason the two other assays described below were used to evaluate the ability to produce apoptosis in cells though cold exposure in the non-necrotic temperature range.

Materials and Methods

Materials: Human coronary artery endothelial cells and rat arterial smooth muscle cells were used in these experiments, and were maintained in culture as previously described. For these assays, the freezing experiments were performed with adherent cell populations. To prepare samples for experimentation., cells were seeded on 22 mm diameter round, culture treated, Thermanox coverslips, which were incubated with growth media in tissue culture plates.

Methods: TUNEL experiments: Like gel electrophoresis, the TUNEL (terminal deoxynucleotidyl transferase mediated dUTP nick end labeling) assay uses DNA fragmentation as the marker for apoptosis. This assay is based on the principle that cleavage of genomic DNA during apoptosis yields single strand breaks ("nicks"), which can be identified by labeling free 3'-OH termini with modified nucleotides in an enzymatic reaction. Incorporated fluorescein is detected by anti-fluorescein antibody Far fragments from sheep, conjugated with horse-radish peroxidase (POD). After substrate reaction to produce a colorimetric precipitate, stained cells can be analyzed under light microscopy.

The adherent samples were frozen by placing the coverslips on pre-cooled glass microslides positioned on the low temperature stage. Solidification was visually observed. To thaw, the coverslips were removed from the stage and dipped in growth medium at 37° C. Temperatures of +5 to −15° C., an exposure time of 60 seconds, and a single freeze/thaw cycle were applied. After thawing, the cover slips were returned to the culture plates, and incubated with growth media at 37° C. Post freeze incubation times of 0, 0.5, 1, 2, 3, 4, and 24 hours were tested, since the time required for apoptotic cells to reach the DNA fragmentation stage was unknown.

After the post-freeze incubation period, the adherent cells were air dried, fixed in a 4% paraformaldehyde solution, and incubated with a 0.3% $H_2O_2$ methanol solution to block endogenous peroxidase. Next, the cells were incubated in a permeabilisation solution to permit penetration of the TUNEL enzyme in a subsequent step. Finally, the cells were incubated in converter horse-radish peroxidase (POD) which binds to TUNEL labeled DNA strand breaks, and then in a DAB/metal enhanced substrate, which produced a dark brown precipitate in the presence of bound POD. The coverslips were rinsed thoroughly with phosphate buffered saline between each of the incubations. After the final incubation in the DAB substrate, the cover slips were analyzed under light microscopy. Hemotoxylin was applied as a counterstain in order to facilitate the count of non-apoptotic cells. A positive control, included in each experiment., was prepared by incubating a fixed, permeabilized cell sample with DNase I to induce DNA strand breaks. Additionally, a sham operated control sample which was exposed the same handling but not to any cold shock, was included in each experiment. In examining the samples, care was taken to confirm that all positively stained cells included in the count of apoptotic cells exhibited a morphology characteristic of apoptosis. These cells appeared shrunken or condensed, in contrast to the swollen, distorted appearance of necrotic cells.

Annexin V experiments: An early event in the process of apoptosis is the flipping or inversion of the molecules of the plasma membrane, causing phospholipid phosphatidylserine (PS) to be translocated from the inner leaflet of the membrane to the outer cell surface. The exposed PS serves as an identification tag utilized by Annexin V, a protein with a high affinity for phosphatidylserine. When apoptotic cells with exposed PS are incubated with the Annexin V compound, the Annexin binds to the PS on the membrane surface. The Annexin V bound sites are labeled with a secondary conjugate, and then prepared for analysis with a substrate reaction that yields a colorimetric change visible to light microscopy.

The freezing of adherent cells on coverslips using the low temperature stage was performed as in the TUNEL experiments. Again, temperatures of +5 to −15° C., and a single freeze/thaw cycle were applied. The correlations established by the TUNEL data demonstrated that the process of apoptosis is underway and has progressed to the DNA fragmentation stage between 1 to 2 hours after cold shock. Since membrane inversion is an earlier event in the apoptotic process, an incubation time of 1 hour was selected for this study. This timing allowed the membrane alterations to be detected before extensive degradation of the cells into smaller bodies could occur. In the Annexin studies, the correlation between cold exposure time and apoptosis was also investigated. Since only short exposure times were relevant to this particular application, cold exposure times of 30, 60, and 120 seconds were tested.

The Annexin assay was performed through the following series of steps. After the one hour incubation, the coverslips were removed from the culture plates and rinsed in phosphate buffered saline. They were then incubated in the Annexin-V-Biotin working solution. Subsequently, the cells were air dried, fixed in a methanol/ethanol solution, air dried again, and then incubated with Streptavidin conjugated with horse radish peroxidase (POD). The Streptavidin labeled the bound Annexin, and the POD provided a colorimetric reaction induced by exposure to a DAB/metal enhanced substrate. Following the substrate reaction, the coverslips were mounted on slides and examined under light microscopy.

Since membrane integrity is lost in necrotic cells, the Annexin V is able to penetrate into those cells, binding to the PS on the inner leaflet of the membrane, and positively staining the necrotic cells. Therefore simultaneous staining with trypan blue was required to differentiate between necrotic and apoptotic cells. Note that although apoptotic cells undergo membrane inversion, the membrane remains intact and impermeant to exclusion dyes such as trypan blue. For each experimental condition, two samples were identically cold shocked. One of these samples was stained with the Annexin protocol as described above. The other sample was stained with trypan blue exclusion dye for 5 minutes and then examined under light microscopy to establish the percentage of necrotic cells induced by each thermal condition. This percentage was subtracted from the percentage of Annexin stained cells, to generate the percentage of apoptotic cells in each sample.

The plots in FIGS. 11A through 11F represent the findings of these assays. FIGS. 11A and 11B show the percentage of apoptotic cells found in samples of human coronary artery endothelial cells and rat arterial smooth muscle cells respectively, as a function of the final temperature to which they were frozen. TUNEL results are indicated with a dashed line, and Annexin results are indicated with a solid line. A minimum of three experiments were conducted for each thermal condition, and the data points represent the averaged result. These plots show that significant levels of apoptosis were found with both assays for the temperature range examined here. The two cell types experience very similar levels of apoptosis in response to the cold shock. For both cell types, apoptosis was not found at hyperthermic conditions (+5 to 0° C.), but was induced at lower temperatures, with a maximum response occurring at −10° C. A comparison between the Annexin results and TUNEL data reveals that the TUNEL assay produced somewhat higher levels of positive staining. It should be noted that, whereas positive apoptosis results are difficult to obtain with the electrophoresis assay, the TUNEL assay has a tendency to be biased towards positive outcomes. One possible factor contributing to falsely high apoptotic results is the positive staining of necrotic cells. The TUNEL reaction preferentially labels DNA strand breaks generated during apoptosis, however extensive DNA fragmentation may occur in late stages of necrosis leading to some positive staining of necrotic cells. Although examination of the morphology of stained cells generally allowed discrimination between necrotic and apoptotic cells, in some fraction of the stained cells the morphological characteristics were inconclusive and the designation of the cells was uncertain.

FIG. 11C shows the relationship between TUNEL detected levels of DNA fragmentation and post freeze incubation time for human coronary artery endothelial cells. The cold exposure consisted of 60 second, single cycle freezes, and the results for three different final temperatures (−5, −10, and −15° C.) are presented in this plot. From the figure it is evident that for each temperature, the maximum response measured by the TUNEL assay was found within 1 to 2 hours after the cold shock. 24 hours after cold shock, little fragmentation was found. This indicates that DNA fragmentation reaches its peak at approximately 2 hours after the apoptotic process begins.

FIGS. 11D and 11E show the relationship between the level of apoptosis detected with the Annexin assay and the time of cold exposure for human coronary artery endothelial cells and rat arterial smooth muscle cells, respectively. In each plot, results for cold shock at −5 and −10° C., in a single freeze cycle with a one hour post freeze incubation are presented. The figures reveal that the time of exposure does not significantly affect the percentage of apoptotic cells, within the 2 minute time range relevant to this application. The small variations in percentage of apoptosis are well within the range of accuracy of the Annexin assay.

In conclusion, the varied results of the three assays reflect the complex nature of the apoptotic phenomenon. Although the electrophoresis assay failed to positively identify a substantial apoptotic fraction, both the TUNEL and the Annexin assays demonstrated some contribution of apoptosis in the overall response of arterial cells to cold shock. The two assays consistently revealed an apoptotic peak at −10° C., and no apoptosis above −5° C. Notwithstanding the limitations in the assays themselves, exact percentages for apoptosis are difficult to establish because of the complexity of the mechanism. Any number of uncontrolled biological factors, including the precise growth phase of the cells, and the biological responsiveness and function of the cells, could affect the initiation of the apoptotic process in an unknown way. This data should therefore be viewed as evidence that significant levels of apoptosis can be induced by cold exposure in the non-necrotic temperature range. Although the qualitative correlations between temperature, time, and peak apoptosis are reliable, the quantitative measurements should be considered approximations.

Experimental II

Cryogenic Intravascular Treatment for Inhibition of Neointimal Formation in the Balloon Injury Model Objectives: The proliferative and morphometric response in the swine coronary model were compared after balloon injury to balloon injury and intravascular cryogenic treatment.

In the rabbit carotid model, percent stenosis in cryogenically treated arteries was compared to sham arteries.

Methods: Seven pigs were treated with balloon overstretch (balloon to artery ratio 1.3:1) in at least two coronary arteries. Intravascular cryogenic treatment was administered in at least one of the arteries after overstretch using a cooled angioplasty balloon. BrdU was administered and the animals were sacrificed on day 7.

Two rabbits (total eight sites in the carotid arteries) were treated with a cooled or non-cooled angioplasty balloon. None of the rabbit carotids received balloon overstretch. The rabbits were sacrificed at 28 days.

Results: In the swine, BrdU index in the sham measured 16% to 43% medial fracture 0% to 67.6%, and percent stenosis 0% to 36.6%. In the cryogenically treated arteries BrdU index measured 18% to 36%, medial fracture 0% to 44.5% and percent stenosis 1.9% to 16.9%.

In the rabbits, percent stenosis measured 3.5% to 10% in the shams and 3.1% to 7.4% in the cryogenically treated arteries. Medial fracture measured 0% in the shams and 0% to 2.4% in the cryogenically treated arteries.

Conclusion: Intravascular cryogenic treatment in the swine and rabbit vascular model effect cell proliferation and present stenosis following a balloon injury.

Materials and Methods

Description of the Intravascular Cryogenic Treatment System: The intravascular cryogenic treatment system includes a cryogenic balloon catheter and a delivery system. The cryogenic balloon catheter (60-cm usable length) was mounted coaxially around a polyimide diffuser tube (0.034" OD.×0.001" wall) and a 0.020" O.D. polyimide tube defining a guide wire lumen. A polyethylene balloon (4 cm in length) was mounted on a polyethylene catheter shaft (048" I.D.×0.005' wall). A manifold is mounted to the proximal end of the balloon shaft and provides ports for guide wire insertion, refrigerant inlet and refrigerant exhaust.

The polyimide diffuser tube connects the most distal end of the balloon to the manifold. The portion of the diffuser tube inside the balloon was fenestrated (40 holes, 0.0028" dia. spaced evenly over 2 cm) to allow refrigerant to flow radially outward against the inside wail of the balloon. The polyimide refrigerant inlet tube (0.011" O.D.×0.001" wall) resides in the coaxial space between the guide wire tube and the diffuser tube.

The refrigerant inlet tube, guide wire tube, balloon shaft and diffuser tube are potted into the manifold using a medical grade adhesive (Dymax 204-CTH). The refrigerant exhaust port, connects to an adjustable pressure relief valve and provides for control of the pressure inside the balloon. The valve is set between 60 and 120 psi.

The delivery system dispenses liquid nitrous oxide through the inlet port on the manifold. The nitrous oxide is contained in an 8-gram cylinder (675 psi at 23° C.) and is inverted so that the refrigerant flows through the inlet port of the manifold. A hand held housing surrounding the liquid nitrous oxide cylinder incorporates a puncture needle and seal on one end and a threaded plunger on the other end, enables the user to safely puncture the gas cylinder. A high-pressure stopcock containing a 20µ filter to trap particulates that may clog the inlet port, is mounted to the to the outlet of the delivery system.

Description of the Temperature Monitoring Guide Wire: A 0.014" coronary guide wire (ACS Extra S'port) was modified to measure temperature at the vessel wall during the cryogenic treatment. A thermocouple (type 'T' and constructed from 0.0015" bifilar wire coated with 0.0001" polyurethane) was mounted 2 cm from the distal tip of the guide wire, covered with 1 cm of polyester (0.00025" thick) and potted with adhesive to displace any air trapped adjacent to the thermocouple.

Operation of the Intravascular Cryogenic Treatment System: After the balloon catheter and the thermocouple wire were positioned at the treatment site, the nitrous oxide cylinder was punctured with the stopcock in the "off" position. The delivery system was then connected to the inlet port on the manifold and the stopcock opened. The nitrous oxide passed through the inlet tube into the diffuser tube, spraying radially outward against the inner surface of the balloon. The nitrous oxide evaporated in the balloon and was exhausted as a gas through the coaxial space between the diffuser tube and the balloon shaft.

Swine Preparation and Treatment: Seven swine (35 to 50 kg) received Aspirin and Ticlid the day prior to the procedure and daily for seven days after the procedure. The animals were sedated and intubated. After placement of an 8F-introducer sheath in the left carotid artery by surgical cut-down, each animal received a dose of heparin. An 8F Cordis H-Stick guiding catheter was placed in the coronary ostium and a 0.014" coronary guide wire was advanced to the artery to be treated. The coronary arteries were imaged using a 2.9F or 3.2F (30 MHz) intravascular ultrasound catheter (IVUS) to identify appropriate treatment sites (diameters ranging from 2.25 mm to 3.75 mm). Fifteen arteries were treated with balloon overstretch injury, 1.3:1 (3 inflations for 30 sec., separated by 1 min. deflation periods to restore coronary perfusion) following either cryogenic or sham treatment using the intravascular cryogenic treatment system with the temperature monitoring guide wire positioned between the balloon and the vessel wall. The sham arteries were treated using treatment catheters filled with saline at pressures similar to cryogenic pressures used. All animals were recovered and survived for seven days. BrdU injections (50 mg/kg) were administered twenty-four hours and one hour prior to sacrifice. Prior to euthanasia all animals were systemically heparinized. The coronary arteries were perfusion fixed at 75 mm Hg for 20 minutes with 10% neutral buffered formalin. The hearts were removed and immersion fixed for at least 24 hours.

Rabbit Preparation and Treatment: Two Rabbits (4.5 and 5 kg) prepared in a similar fashion were treated with the intravascular cryogenic treatment system or sham catheter in the carotid artery. Both femoral arteries were accessed to accommodate the 4.5F treatment catheter (or sham catheter) and the temperature monitoring guide wire. The rabbits were survived and sacrificed on day 28. The carotid arteries were perfusion fixed with 10% neutral buffered formalin.

RESULTS TABLE I

| Animal | Animal # | Artery | ° C./Time (sec) | % Stenosis | % Medical Fracture | BrdU % (neointimal) |
|---|---|---|---|---|---|---|
| Swine | 42 | LAD | −13/17 | 1.4 | 36.3 | 18 |
| Swine | 42 | LCX | sham | 8.3% | 27.5 | 43 |
| Swine | 24 | LAD | −31/24 | 10.6 | 44.5 | 24 |
| Swine | 24 | LCX | sham | 24.4 | 34.9 | 26 |
| Swine | 61 | LCX | −18/18 | 13.5 | 24.1 | 31 |
| Swine | 61 | RCA | sham | 36.6 | 67.6 | 24 |
| Swine | 9001 | LCX | −28/24 | 1.9 | 0.0 | not measured |
| Swine | 9001 | LAD | sham | 17.3 | 41.9 | 16 |
| Swine | 9002 | LAD | −21/30 | 9.36 | 38.1 | 36 |

RESULTS TABLE I-continued

| Animal | Animal # | Artery | °C./Time (sec) | % Stenosis | % Medical Fracture | BrdU % (neointimal) |
|---|---|---|---|---|---|---|
| Swine | 9002 | LCX | sham | 0.0 | 0.0 | not measured |
| Swine | 9005 | LCX | −11/9 | 16.9 | 28.21 | 24 |
| Swine | 9005 | LAD | sham | 12.3 | 28.1 | 29 |
| Swine | 9006 | LAD | −12/6 | 4.6 | 30.6 | 31 |
| Swine | 9006 | LCX | sham | 15.3 | 51.9 | 26 |
| Rabbit | 2997K | Left-prox | sham | 10.0 | 0.0 | N/A |
| Rabbit | 2997K | Left-mid | −15/23 | 7.4 | 2.4 | N/A |
| Rabbit | 2997K | Right-prox | sham | 9.2 | 0.0 | N/A |
| Rabbit | 2997K | Right-mid | −21/25 | 5.4 | 0.0 | N/A |
| Rabbit | 3131K | Left-prox | sham | 5.7 | 0.0 | N/A |
| Rabbit | 3131K | Left-mid | −33/25 | 3.8 | 0.0 | N/A |
| Rabbit | 3131K | Right-prox | sham | 3.5 | 0.0 | N/A |
| Rabbit | 3131K | Right-mid | +4/0 | 3.1 | 0.0 | N/A |

Conclusions and Discussion

The rabbit data of Results Table I suggests that over a wide range of temperatures (+4 to −33° C.) the cryogenic treatment system did not produce significant stenosis and in all cases produced less stenosis when compared to the sham in the same artery. The cryogenic treatment in the rabbit carotids did no harm and healed in a benign fashion.

In the overstretch swine model of Results Table I, the most striking result was observed in animal 42. The percent medial fracture was highest in the cryogenically treated artery (36.6% in the treated artery compared to 27.5% in the sham) however both the percent stenosis and BrdU index were lower. Overall, the morphometric analysis of treated arteries verses sham arteries revealed a substantial reduction in the percent stenosis as the cryogenic arteries averaged 8.3% verses 16.3% in sham treated arteries.

Experimental III

Swine Coronary Pilot Trial

Purpose: To determine the vascular effects of a freezing treatment in a stent overstretch swine coronary model.

Hypothesis: Endovascular cryothopathy applied to an injured artery will result in similar or less neointimal formation than sham as judged by histologic and morphometric examination at 28 days.

Animal Preparation: Four Yorkshire white pigs weighing 35 to 50 kg were used for this study. On the day prior to the experiment, each pig received Aspirin and ticlopidine. Following general anesthesia, the left carotid artery of each animal was cleanly dissected and an 8 Fr. sheath was placed. Systemic anticoagulation was achieved with intravenous heparin.

After each experiment, the left carotid artery was repaired and the animal was recovered from anesthesia. Animals were housed on standard chow for 28 days following the experiments. For the duration of the recovery period the animals received Aspirin, and ticlopidine was given for the first two weeks. On day 28, each animal was sacrificed in an ethical manner, and the heart was perfusion fixed at approximately 75 mm Hg for 20 minutes in 10% buffered formalin. The arterial segments of interest were harvested and the tissue underwent routine histologic and morphometric evaluation.

Device Description: The intravascular cryogenic treatment system included a cryogenic balloon catheter, as shown in FIGS. 7 and 7A, and a delivery system. The cryogenic balloon catheter 110 (60 cm usable length) was mounted coaxially around a polyimide fluid delivery tube 112 (0.011" I.D. by 0.001" wall) and a 0.020" O.D. polyethylene tube defining a guide wire lumen 114. A polyethylene balloon 116 (3 cm in length) was mounted on a polyethylene catheter shaft (0.165" I.D. by 0.005" wall). A manifold 118 was mounted to the proximal end of the balloon shaft and provided ports for guide wire insertion, refrigerant inlet, refrigerator exhaust, and temperature measurement inside the balloon.

The guide wire tube connected the most distal end of the balloon to the manifold. The portion of the delivery tube inside the balloon, mounted coaxially around the guide wire lumen, allowed refrigerant to flow evenly against the inside wall of the balloon. The polyimide refrigerant inlet tube 123 (0.011" O.D. by 0.001" wall) resided in the coaxial space 119 between the guide wire tube 114 and balloon catheter shaft 110.

A "K" type thermocouple 120 constructed from a 0.0015" by 0.003" bifilar wire was mounted inside the balloon. The thermocouple wire leads 117 were positioned in the annular space between guide wire lumen 114 and balloon catheter shaft 110. A connector 121 was mounted on manifold 118.

The refrigerant inlet tube 123, guide wire tube 114, balloon shaft 110, and thermocouple wires 120 were ported into manifold 118 using a medical grade adhesive (Dymax 204-CTH). The refrigerant exhaust port 122 connected to an adjustable pressure relief valve 124 and provided for control of the pressure inside the balloon. The valve was set at 15 psi.

The delivery system dispensed liquid AZ-50 126 (pentafluorothane and trifluoroethane) through the inlet port on the manifold. The AZ-50 was contained a 25 cc cylinder (330 psi at 23° C.) and was inverted so that the refrigerant flowed through the inlet port of the manifold.

Experimental Methods: A guide catheter was advanced to the route of the aorta and the coronary arteries were selectively engaged under fluoroscopic visualization. Each coronary artery was interrogated by IVUS to determine cross-sectional diameter. Arterial injury was induced by percutaneous catheter implantation of intracoronary stents at a stent-to-artery ratio of 1.0:1 in one animal (#9108) and 1.3:1 in the other three animals (Nos. 9195, 9196, and 9197). Following stent placement, one artery in each animal underwent freezing treatment by insertion of the cryogenic catheter (described above), with the treatment zone centered in the stent. Refrigerant was delivered in to the catheter for a period of 30 seconds, producing balloon inflation at a pressure of 15 psi, and a temperature of −10° C. at the balloon/artery interface. Cryogenic catheter sizes were chosen to provide good apposition between the balloon and the artery wall. The other artery in each animal was sham treated at the stent location using a balloon catheter identical to the cryogenic catheter, but delivering no temperature change, inflated at 15 psi for 30 seconds.

Results: All animals underwent routine histologic evaluation. The endpoint of the study lay in a comparison of the lumen area, neointimal area, and percent stenosis in sham treated arteries versus cold treated arteries. Results Table II contains the data. Mean values shown in the bottom rows indicate that cryotherapy produces less neointimal growth and lower percentage stenosis than observed in sham treated arteries.

RESULTS TABLE II

| Animal # | Vessel | Treatment | Medical Area | Neointimal Area | Lumen Area | % Stenosis | % Medical Fracture | Injury Score |
|---|---|---|---|---|---|---|---|---|
| 9108 | LAD | cryo | 1.43 | 2.03 | 3.42 | 37.25 | 0. | 0.88 |
| 9108 | LCX | sham | 1.25 | 3.45 | 2.25 | 60.53 | 0. | 0.55 |
| 9195 | LCX | cryo | 1.46 | 5.29 | 3.32 | 61.44 | 15.76 | 0.56 |
| 9195 | LAD | sham | 1.58 | 6.31 | 2.02 | 75.75 | 15.47 | 0.83 |
| 9196 | LAD | cryo | 1.57 | 2.92 | 3.17 | 47.95 | 0. | 0.08 |
| 9196 | LCX | sham | 1.52 | 2.16 | 3.61 | 37.44 | 0. | 0.17 |
| 9197 | RCA | cryo | 1.38 | 5 10 | 3.82 | 57.17 | 21.45 | 0.58 |
| 9197 | LAD | sham | 2.00 | 6.67 | 3.39 | 68.30 | 23.87 | 0.92 |
| Mean | CRYO | cryo | 1.46 | 3.83 | 3.43 | 50. | 9.84 | 0.525 |
| Mean | SHAM | sham | 1.59 | 4.65 | 2.82 | 60. | 9.3 | 0.617 |
| P-Value | | | 0.45 | 0.57 | 0.22 | 0.29 | 0.46 | 0.71 |

(* areas are given in mm$^2$)

Experimental IV

A study was performed to determine if endovascular cryotherapy reduces late neointimal formation in a porcine coronary model of in-stent restenosis. Normolipemic juvenile swine underwent overstretch balloon angioplasty and stenting. About 4 weeks after this initial angioplasty in-stenting, the in-stent lesions were treated with endovascular cryotherapy or a placebo/sham treatment followed by a secondary stenting. Animals were non-randomly allocated to the active treatment group (for treatment at a tissue treatment of −5° C.) or the placebo/control group as outlined in Table III below:

TABLE III

TREATMENT GROUPS

| Animal | Vessel | Group | Temperature | Volume and Concentration |
|---|---|---|---|---|
| 526 | LAD | I | −5° C. | |
| 526 | LCX | II | 37° C. | 0 |
| 526 | RCA | I | −5° C. | |
| 527 | LAD | II | 7° C. | 0 |
| 527 | RCA | I | 5° C. | |
| 528 | LAD | I | 5° C. | |
| 528 | RCA | II | 37° C. | 0 |
| 529 | LAD | II | 37° C. | 0 |
| 529 | LCX | I | 5° C. | |
| 529 | RCA | I | −5° C. | |
| 530 | LAD | I | −5° C. | |
| 530 | RCA | II | 37° C. | 0 |
| 530 | LCX | I | −5° C. | |
| 531 | LAD | II | 37° C. | 0 |
| 531 | RCA | I | −5° C. | |

In-stent lesions were treated with appropriately sized (one-to-one stent to artery ratio) balloon expandable stainless steel stents (Duet™, 18 or 23 mm long, 3.0 to 24.0 mm diameter) to achieve a less than 10% angiographic residual stenosis. Angiographic and intravascular ultrasound analysis were performed after about 28 days, and histological analysis was completed thereafter as described hereinbelow.

The animals generally had weights between about 20 and 50 kg, and were given pre-operative Aspirin (650 mg) and Procardia XL (30 mg) with a small amount of food. After sedation with about 20 mg/kg Ketamine HCL and Xylazine (2 mg/kg), the animals were intubated and mechanically ventilated with intravenous access established via an ear vein. Adjunctive atropine (0.5 to 1.0 mg IV) was administered as indicated. Continuous anesthesia was maintained with 1% to 2% isoflurane. Sodium pentobarbital was administered as needed.

A carotid artery cut-down was performed to gain arterial access. Baseline coronary angiography was performed with an 8F guiding catheter after the administration of 150 units/kg of intra-arterial Heparin. Additional Heparin was provided so as to maintain the activated clotting time above 300 seconds.

Two hundred micrograms of nitroglycerin were administered intracoronary to prevent vasospasm following overstretch balloon angioplasty. The vessel targeted for treatment was sized by visual estimate using the guiding catheter as a reference. Overstretch balloon injury was completed using a standard balloon angioplasty catheter having a size between about 1.2 and 1.4 times the baseline vessel diameter.

Coronary angiography was completed after balloon angioplasty. A 3.0 to 4.0 mm diameter stainless steel balloon expanded stent with a length between 13 and 18 mm was implanted at the overstretch site using a single balloon inflation at 8 to 14 atm. Coronary angiography was completed again after stent deployment. The catheters and sheath were removed and the carotid artery was treated using standard techniques. The treated animals were allowed to recover from the procedure and received 325 mg of Aspirin daily while remaining on a normal diet.

As outlined in Table III, the treatment vessels included the left anterior descending artery LAD, the left circumflex artery LCX, and the right coronary artery RCA. The timing of the initial stent injury, cryotherapy or sham treatment, and follow-up are shown in the animal log provided in FIG. 12A.

For the endovascular cryotherapy treatment itself baseline coronary angiography was performed with an 8F guiding catheter after administration of intra-arterial Heparin. Activated clotting time was maintained at over 300 seconds, with 200 micrograms of nitroglycerin administered intracoronary. The vessels to be treated were sized by a visual estimate using the guiding catheter as a reference.

The cryotherapy was administered using a cooled balloon as described hereinabove. A 3.0 to 4.0 mm diameter, 13 to 18 mm long stainless steel balloon expandable stent was implanted at the treatment site (within the prior stent) using a single balloon inflation at between 8 and 14 atm. Coronary angiography was completed after stent deployment.

After completion of stenting, intravascular ultrasound was performed by tracking a 30 MHz transducer (CVIS™, from Scimed, of Maple Grove, Minn.) over the guidewire within a 3.2F imaging catheter. Images were recorded using a motorized pullback rate of 0.5 mm/sec for off-line analysis. This process was completed in an additional artery for the placebo treatment. Following intravascular ultrasound, the catheters and sheath were removed and the carotid artery treated using standard techniques. The animals were recovered and monitored, receiving 250 mg of Ticlid for 14 days and 325 mg of Aspirin with a normal diet.

Each angiogram was evaluated for evidence of intraluminal filling defects, side branch occlusion, lumen narrowing, and distal coronary flow characteristics. The baseline, balloon inflated stent, post injury, and follow-up coronary artery minimal lumen diameters were measured from non-overlapped and non-foreshortened views using the guiding catheter for image calibration, and the data was recorded in mm. The acute balloon-to-artery ratio (minimal balloon inflated diameter divided by the baseline lumen diameter) was calculated from this data for each treated vessel. The percent stenosis at follow-up, defined as: [(mean reference lumen diameter minus minimal lumen diameter at follow-up/mean reference lumen diameter)]×100, was also calculated.

Follow-up angiography and intravascular ultrasound were performed at about 28 days after the cryotherapy (or sham treatment) and stenting using the same techniques described above. The animals were then euthanized, and the heart was removed immediately with the coronary arteries pressure perfused with formalin at 60 to 80 mm Hg for one hour. Histological evaluation was then performed.

Quantitative analysis of the treatment is provided in FIG. 12B. Measurements are generally broken up into measurements for the entire group of test animals (Total), measurements for the control vessels which received only placebo/sham treatments (Control) and measurements for the arteries which received cryotherapy as described above (Cryo). As described, above baseline (BL) measurements were taken before treatment, while additional measurements were taken after the initial balloon injury (Balloon). The final two group of measurements were taken after cryotherapy or the associated placebo/sham (Post Ref), and at the follow-up date (FU). In addition to the basic reference diameter measurements, minimum lumen diameters (MLD) and percent diameter stenosis (%DS) are also set forth in FIG. 2B.

Statistical analysis of the test group was performed using Statview 4.5 (from Abacus of Berkeley, Calif.), the summary of which is provided in FIG. 12C. Morphological data are compared by analysis of variance (ANOVA) testing. Fischer's protected least significant difference (PLSD) is shown in FIG. 12C, in which a level of probability of statistical significance is indicated by $p<0.05$ (at which the results could be considered to have established statistical significance).

From the data illustrated in FIGS. 12B and 12C, it can be seen that the follow-up percent diameter stenosis for the arteries treated with cryotherapy is over 17% less than the percent diameter stenosis for the sham treated arteries in the control group. This represents a decrease in actual or observed stenosis of over 34% when the control group stenosis is used as the baseline.

While the exemplary embodiments have been described in some detail by way of example and for clarity of understanding, a variety of changes, adaptations, and modifications will be obvious to those of skill in the art. Hence, the scope of the present invention is limited solely by the appended claims.

What is claimed is:

1. A method for treating a blood vessel region, the method comprising:
   dilating the blood vessel region;
   cooling an inner surface of the blood vessel region to a temperature in a range from about 5° C. to about 15° C., while dilating the blood vessel region with a balloon, by introducing a cooling fluid into the balloon as a liquid and changing a phase of the cooling fluid to a gas within the balloon so that the cooling fluid inflates the balloon and simultaneoualy cools the blood vessel region, wherein the blood vessel region is cooled such that observed subsequent excessive cell growth induced stenosis of the blood vessel is inhibited.

2. The method of claim 1, wherein the cooling fluid comprises $N_2O$.

3. The method of claim 1, wherein the cooling step is performed so as to cool the inner surface of the blood vessel to about 5° C.

4. The method of claim 1, wherein the cooling step is performed so as to cool the inner surface of the blood vessel to about 10° C.

5. The method of claim 1, wherein the cooling step effects an observed relative reduction of stenosis of at least about 16 % as compared to a stenosis of an equivalently treated uncooled blood vessel region.

6. The method of claim 1, wherein the cooling step is performed so as to induce apoptosis.

7. A method for treating a blood vessel region, the method comprising:
   positioning a balloon of a balloon catheter along the blood vessel region;
   cooling and dilating an inner surface of the blood vessel region by introducing a cooling fluid into the balloon as a liquid and changing a phase of the cooling fluid to a gas within the balloon so that the cooling fluid inflates the balloon and simultaneously cools the blood vessel region, wherein the cooling fluid cools the inner surface of the blood vessel region to a temperature in arange from about 5° C. to about 15° C.

* * * * *